(12) United States Patent
Grill et al.

(10) Patent No.: US 10,744,328 B2
(45) Date of Patent: Aug. 18, 2020

(54) SYSTEM FOR GENERATING AND APPLYING WAVEFORM SHAPES FOR TREATING NEUROLOGICAL DISORDERS OPTIMIZED FOR ENERGY EFFICIENCY

(71) Applicant: Duke University, Durham, NC (US)

(72) Inventors: Warren M. Grill, Chapel Hill, NC (US); Amorn Wongsarnpigoon, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/651,072

(22) Filed: Jul. 17, 2017

(65) Prior Publication Data
US 2017/0312527 A1    Nov. 2, 2017

Related U.S. Application Data

(63) Continuation of application No. 14/796,216, filed on Jul. 10, 2015, now Pat. No. 9,707,397, which is a continuation of application No. 13/118,081, filed on May 27, 2011, now Pat. No. 9,089,708.

(60) Provisional application No. 61/348,963, filed on May 27, 2010.

(51) Int. Cl.
*A61N 1/36* (2006.01)
*A61N 1/05* (2006.01)

(52) U.S. Cl.
CPC ....... *A61N 1/36146* (2013.01); *A61N 1/3606* (2013.01); *A61N 1/36175* (2013.01); *A61N 1/0529* (2013.01)

(58) Field of Classification Search
None
See application file for complete search history.

(56) References Cited

U.S. PATENT DOCUMENTS

| | | | |
|---|---|---|---|
| 3,833,005 A | 9/1974 | Wingrove |
| 4,338,945 A | 7/1982 | Kosugi |
| 4,979,507 A | 12/1990 | Heinz et al. |
| 5,018,524 A | 5/1991 | Gu |
| 5,073,544 A | 12/1991 | Seto |
| 5,095,904 A | 3/1992 | Seligman |
| 5,184,616 A | 2/1993 | Weiss |
| 5,226,413 A | 7/1993 | Bennett et al. |
| 5,485,851 A | 1/1996 | Erickson |
| 5,716,377 A | 2/1998 | Rise |
| 5,724,985 A | 3/1998 | Snell |

(Continued)

FOREIGN PATENT DOCUMENTS

| | | |
|---|---|---|
| CN | 86102850 A | 11/1987 |
| EP | 1145735 | 10/2001 |

(Continued)

OTHER PUBLICATIONS

European Patent Office, European Search Report, EP 17001653, dated Jan. 4, 2018.

(Continued)

*Primary Examiner* — Kennedy Schaetzle
(74) *Attorney, Agent, or Firm* — McDonald Hopkins LLC

(57) ABSTRACT

Systems and methods for stimulation of neurological tissue apply a stimulation waveform that is derived by a developed genetic algorithm (GA), which may be coupled to a computational model of extracellular stimulation of a mammalian myelinated axon. The waveform is optimized for energy efficiency.

7 Claims, 14 Drawing Sheets

- New generation
  - Replace some or all of current population with offspring
- Repeat process until termination criterion met
  - Fixed number of generations OR – Fitness changes by < X%

(56) References Cited

U.S. PATENT DOCUMENTS

| | | | |
|---|---|---|---|
| 6,066,163 A | 5/2000 | John | |
| 6,560,487 B1 | 5/2003 | McGraw | |
| 6,560,490 B2 | 5/2003 | Grill | |
| 6,738,668 B1 | 5/2004 | Mouchawar et al. | |
| 6,879,860 B2 | 4/2005 | Wakefield et al. | |
| 6,934,580 B1 | 8/2005 | Osorio et al. | |
| 6,944,501 B1 | 9/2005 | Pless | |
| 7,010,351 B2 | 3/2006 | Firlik | |
| 7,191,014 B2 | 3/2007 | Kobayashi | |
| 7,321,796 B2 | 1/2008 | Fink et al. | |
| 7,483,747 B2 | 1/2009 | Gilner | |
| 7,949,397 B1 | 5/2011 | Wenzel | |
| 7,970,477 B2 | 6/2011 | Loeb et al. | |
| 8,073,544 B2 | 12/2011 | Pless | |
| 8,355,789 B2 | 1/2013 | Werder | |
| 8,447,405 B2 | 5/2013 | Grill | |
| 8,694,106 B2 | 4/2014 | Pless | |
| 8,798,755 B2 | 8/2014 | Grill | |
| 8,923,981 B2 | 12/2014 | Grill | |
| 9,089,708 B2* | 7/2015 | Grill | A61N 1/36146 |
| 9,242,095 B2 | 1/2016 | Grill | |
| 9,259,579 B2 | 2/2016 | Grill | |
| 9,572,988 B2 | 2/2017 | Grill | |
| 9,744,363 B2 | 8/2017 | Grill | |
| 10,086,204 B2 | 10/2018 | Grill | |
| 10,086,205 B2 | 10/2018 | Grill | |
| 2002/0077670 A1 | 6/2002 | Archer | |
| 2002/0177882 A1 | 11/2002 | Dilorenzo | |
| 2003/0135248 A1 | 7/2003 | Stypulkowski | |
| 2004/0158298 A1 | 8/2004 | Gliner | |
| 2004/0243192 A1 | 12/2004 | Hepp et al. | |
| 2004/0249422 A1 | 12/2004 | Gilner | |
| 2005/0060009 A1 | 3/2005 | Goetz | |
| 2005/0222641 A1 | 10/2005 | Pless | |
| 2005/0228453 A1 | 10/2005 | Havel et al. | |
| 2005/0228461 A1 | 10/2005 | Osorio et al. | |
| 2006/0015153 A1 | 1/2006 | Gliner | |
| 2006/0017749 A1 | 1/2006 | McIntyre | |
| 2006/0111759 A1 | 5/2006 | Hoyme | |
| 2006/0212089 A1 | 9/2006 | Tass | |
| 2007/0067004 A1 | 3/2007 | Boveja et al. | |
| 2007/0198066 A1 | 8/2007 | Greenberg et al. | |
| 2007/0288064 A1 | 12/2007 | Butson | |
| 2008/0045775 A1 | 2/2008 | Lozano | |
| 2009/0036949 A1 | 2/2009 | Kokones | |
| 2009/0082640 A1 | 3/2009 | Kovach | |
| 2009/0110958 A1 | 4/2009 | Hyde | |
| 2009/0131993 A1 | 5/2009 | Rousso | |
| 2009/0264954 A1 | 10/2009 | Rise | |
| 2010/0042194 A1 | 2/2010 | Ayal et al. | |
| 2010/0121407 A1 | 5/2010 | Pfaff et al. | |
| 2010/0121416 A1 | 5/2010 | Lee | |
| 2010/0152807 A1 | 6/2010 | Grill | |
| 2010/0312303 A1 | 12/2010 | York et al. | |
| 2010/0331916 A1 | 12/2010 | Parramon | |
| 2011/0093041 A1 | 4/2011 | Straka | |
| 2011/0106213 A1 | 5/2011 | Davis | |
| 2011/0184486 A1 | 7/2011 | De Ridder | |
| 2011/0196441 A1* | 8/2011 | Ryu | A61N 1/36514 607/17 |
| 2011/0270348 A1 | 11/2011 | Goetz | |
| 2012/0004707 A1 | 1/2012 | Lee | |
| 2012/0016435 A1 | 1/2012 | Rom | |
| 2012/0290041 A1 | 11/2012 | Kim | |
| 2013/0006330 A1 | 1/2013 | Wilder | |
| 2013/0102919 A1 | 4/2013 | Schiff | |
| 2013/0231715 A1 | 9/2013 | Grill | |
| 2013/0345773 A1 | 12/2013 | Grill | |
| 2014/0257428 A1 | 9/2014 | Zhu | |
| 2014/0353944 A1 | 12/2014 | Grill | |
| 2017/0361099 A1 | 12/2017 | De Ridder | |
| 2018/0064944 A1 | 3/2018 | Grill | |

FOREIGN PATENT DOCUMENTS

| | | |
|---|---|---|
| EP | 2766087 | 8/2014 |
| JP | 2008506464 A | 3/2008 |
| WO | WO2006019764 A2 | 2/2006 |
| WO | WO2010039274 | 4/2010 |
| WO | WO2014130071 A1 | 8/2014 |

OTHER PUBLICATIONS

SA/US, International Search Report and Written Opinion prepared for PCT/US2014/072112, dated Apr. 16, 2015.

International Preliminary Report on Patentability for PCT/US11/38416, dated May 3, 2012.

International Search Report/Written Opinion dated Dec. 7, 2011 in International Patent Application No. PCT/US11/38416.

International Search Report and the Written Opinion of the International Searching Authority, PCT/US2013/046183, Duke University, dated Oct. 4, 2013.

International Search Report and the Written Opinion of the International Searching Authority, PCT/US2012/059787, Duke University, dated Jan. 4, 2013.

International Preliminary Examination Report, PCT/US2009/05459, Duke University, dated Jan. 11, 2011.

International Search Report and the Written Opinion of the International Searching Authority, PCT/US2009/05459, Duke University, dated Dec. 3, 2009.

Extended European Search Report, Application No. 09818122.5-1652/2340078, Duke University, dated Aug. 2, 2013.

Rubin, Jonathan et al., High Frequency Stimulation of the Subthalamic Nucleus Eliminates Pathological Thalamic Rhythmicity in a Computational Model, Journal of Computational Neuroscience, vol. 16, pp. 211-235, 2004.

McIntyre, Cameron et al., Cellular Effects of Deep Brain Stimulation: Model-Based Analysis of Activation and Inhibition, J. Neurophysiol, vol. 91, pp. 1457-1469, 2004.

Birdno, Merrill Jay, Analyzing the Mechanisms of Action of Thalamic Deep Brain Stimulation: Computational and Clinical Studies, Ph. D. Dissertation, Department of Biomedical Engineering, Duke University, Durham, NC, USA, Aug. 2009.

Constantoyannis, Constantine, et al., Tremor Induced by Thalamic Deep Brain Stimulation in Patients with Complex Regional Facial Pain, Movement Disorders, vol. 19, No. 8, pp. 933-936, 2004.

Benabid, Alim et al., Long-term suppression of tremor by chronic stimulation of the ventral intermediate thalamic nucleus, The Lancet, vol. 337, pp. 403-406, Feb. 16, 1991.

Davis, Lawrence, Handbook of Genetic Algorithms, Van Nostrand Reinhold, NY, pp. 1-402, 1991.

Dorval, Alan et al., Deep Brain Stimulation Alleviates Parkinsonian Bradykinesia by Regularizing Pallidal Activity, J. Neurophysiol, vol. 104, pp. 911-921, 2010.

Fogelson, Noa et al., Frequency dependent effects of subthalamic nucleus stimulation in Parkinson's disease, Neuroscience Letters 382, 5-9, 2005.

Grefenstette, John, Optimization of Control Parameters for Genetic Algorithms, IEEE Transactions on Systems, Man, and Cybernetics, vol. SMC-16, No. 1, pp. 122-128, Jan./Feb. 1986.

Feng, Xiao-jiang et al., Optimal Deep Brain Stimulation of the Subthalamic Nucleus—a Computational Study, Journal of Computational Neuroscience, 23(3):265-282, Jan. 9, 2007.

Grill, W.M. et al., Effect of waveform on tremor suppression and paresthesias evoked by thalamic deep brain stimulation (dbs), Society for Neuroscience Abstract 29, 2003.

Kuncel, Alexis et al., Clinical Response to Varying the Stimulus Parameters in Deep Brain Stimulation for Essential Tremor, Movement Disorders, vol. 21, No. 11, pp. 1920-1928, 2006.

Kupsch, A. et al., The effects of frequency in pallidal deep brain stimulation for primary dystonia, J. Neurol 250:1201-1205, 2003.

Tinnerman, Lars et al., The cerebral oscillatory network of parkinsonian resting tremor, Brain, 126, pp. 199-212, 2003.

(56) References Cited

OTHER PUBLICATIONS

Limousin, Patricia et al., Effect on parkinsonian signs and symptoms of bilateral subthalamic nucleus stimulation, The Lancet, vol. 345, pp. 91-95, Jan. 14, 1995.
Brocker, David. et al., Improved Efficacy of Temporally Non-Regular Deep Brain Stimulation in Parkinson's Disease, Department of Biomedical Engineering, Duke University, Durham NC 27708-0281, pp. 1-34. 2012.
Extended European Search Report for Application 13875748.9 PCT/US2013046183, dated Mar. 9, 2016, European Patent Office, Germany.
International Searching Authority, US Patent Office; International Search Report and Written Opinion for PCT/US2014/038809, dated Dec. 15, 2014, 19 pages.
Feng et al. "Toward closed-loop optimization of deep brain stimulation for Parkinson's disease: concepts and lessons from a computational model." J. Neural Eng. 4 (2007) L14-L21. Feb 23, 2007.
So et al. "Relative contributions of local cell and passing fiber activation and silencing to changes in thalamic fidelity during deep brain stimulation and lesioning: a computational modeling study". Comput Neurosci (2012) 32:499-519. Oct. 5, 2011.
Kent et al. "Instrumentation to Record Evoked Potentials for Closed-Loop Control of Deep Brain Stimulation". Conf Proc IEEE Eng Med Biol Soc. 2011; 2011: 6777-6780. doi:10.1109/IEMBS.2011.6091671.
Dorval et al. "Deep Brain Stimulation that Abolishes Parkinsonian Activity in Basal Ganglia Improves Thalamic Relay Fidelity in a Computational Circuit". Conf Proc IEEE Eng Med Biol Soc. 2009; 1: 4230. doi:10.11091EMB5.2009.5333611.
European Patent Office, Supplementary European Search Report, EP14874436, dated Jan. 17, 2018.

\* cited by examiner

Population:
Finite number of candidate solutions

Organism:
A candidate solution

Genes:
Parameters of a candidate solution

Fitness:
Associated with each candidate solution. Based on cost function to be optimized.

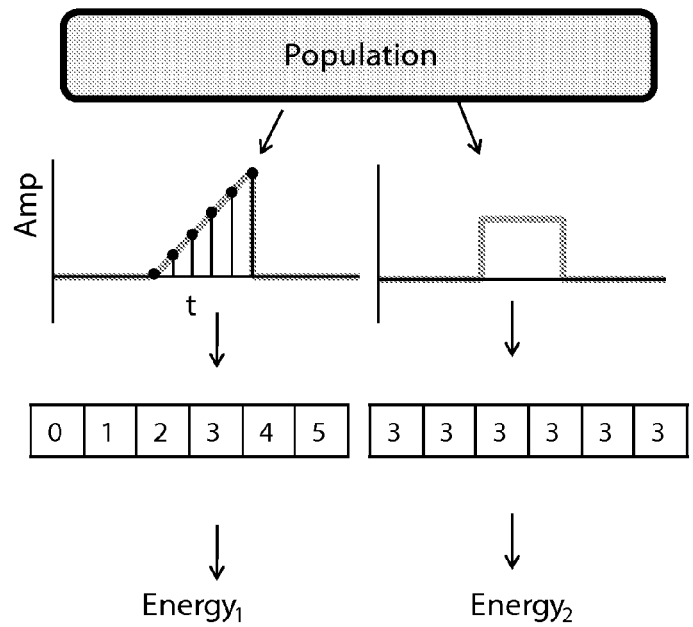

*Fig. 4A*

After evaluating fitness in each 'generation'

- 'Mating' and 'mutations': Promote wider exploration of solution space.
  - Parents may be selected based on fitness

- 'Selection': Pushes search towards superior solutions.
  - Parents
  - Organisms to survive to next generation

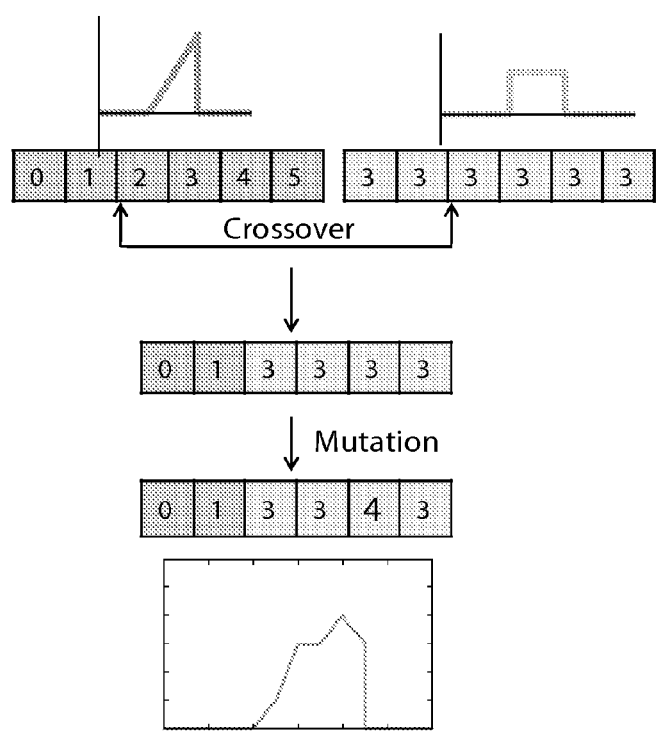

*Fig. 4B*

- New generation
  - Replace some or all of current population with offspring
- Repeat process until termination criterion met
  - Fixed number of generations OR – Fitness changes by < X%

Compartmental model of single mammalian axon

Hodgkin-Huxley

Sweeney

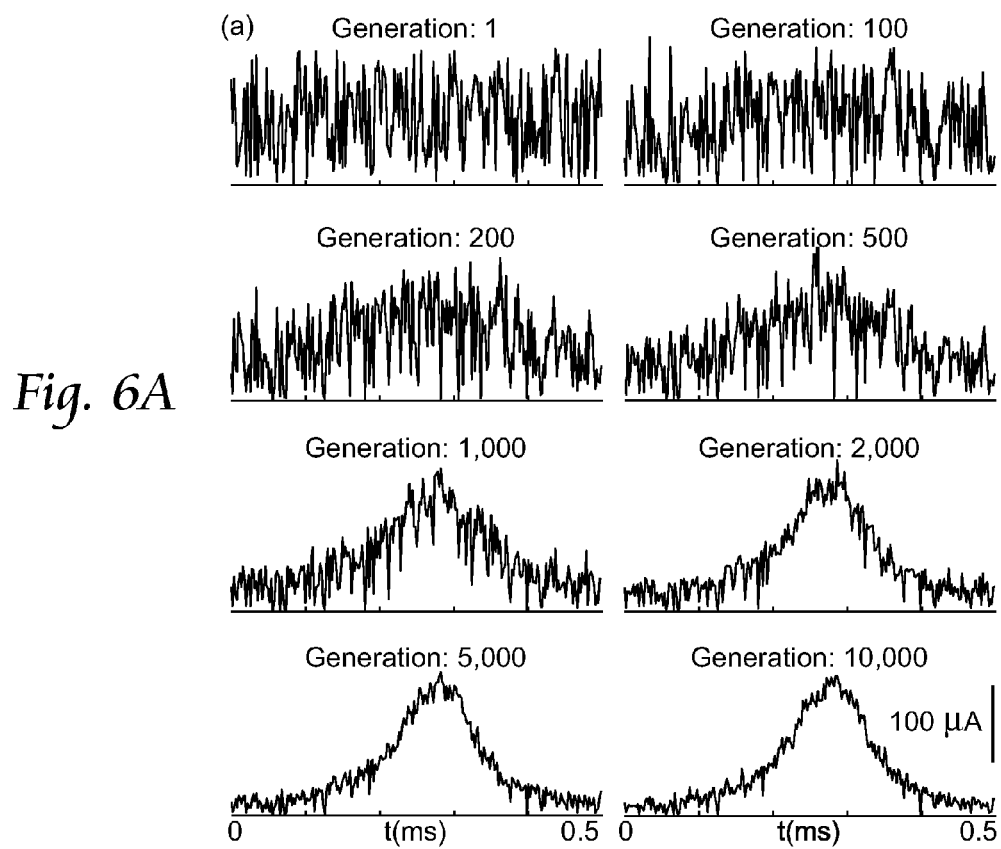
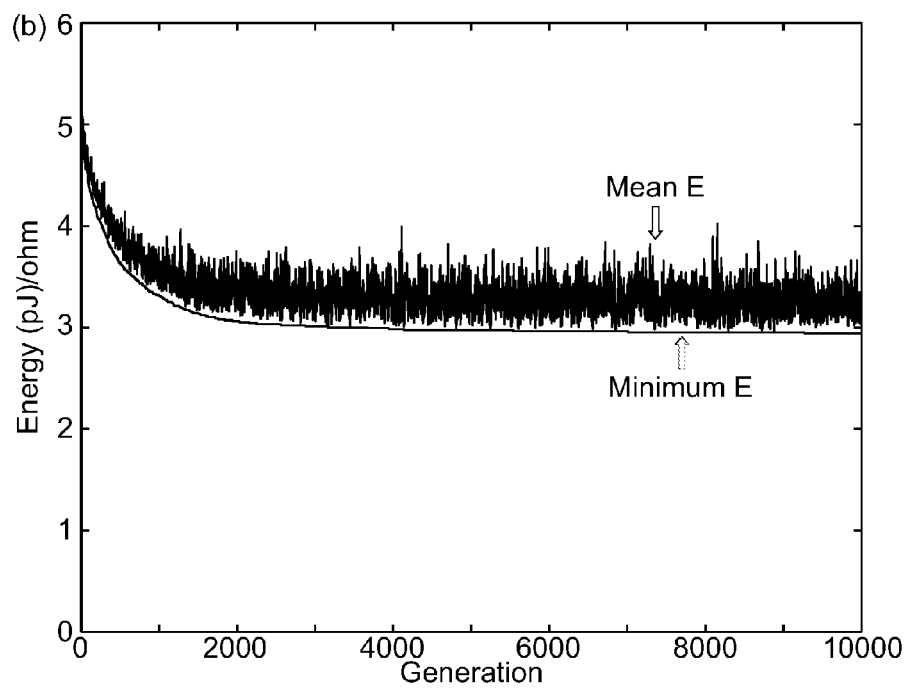
Fig. 6A
Fig. 6B

*Fig. 10A*
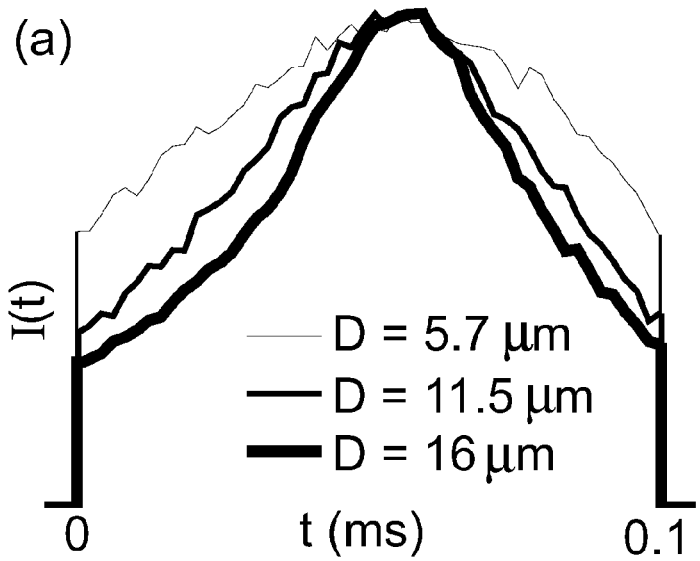
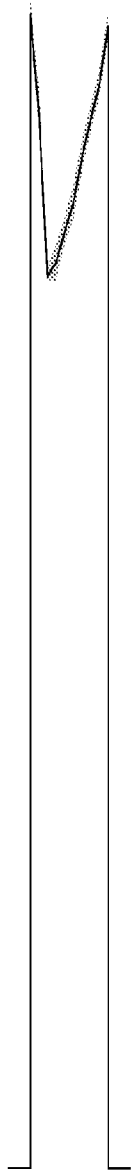
*Fig. 10B*
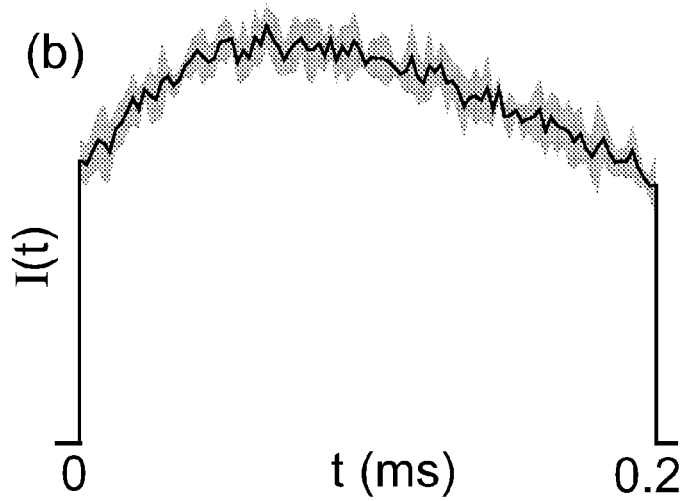
PW = 0.02 ms
*Fig. 10C*

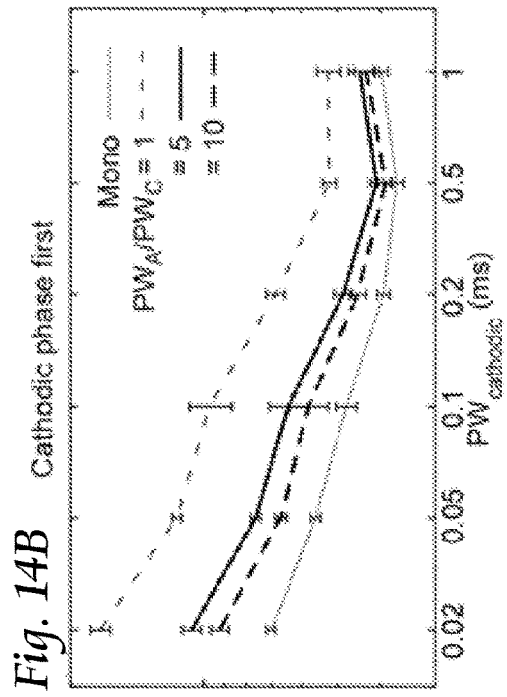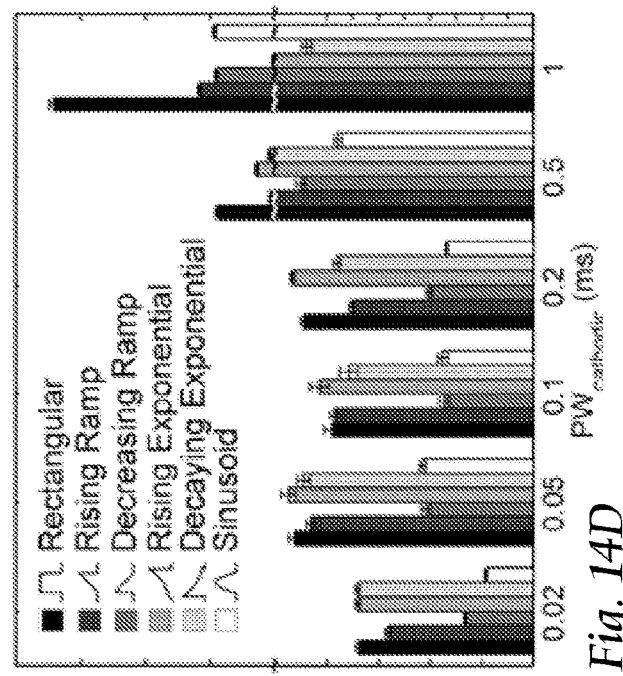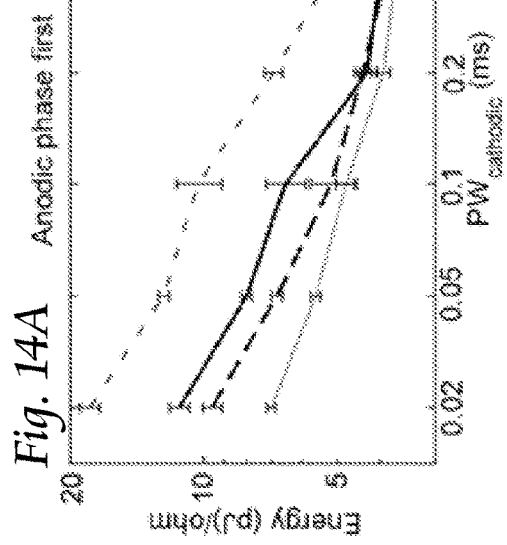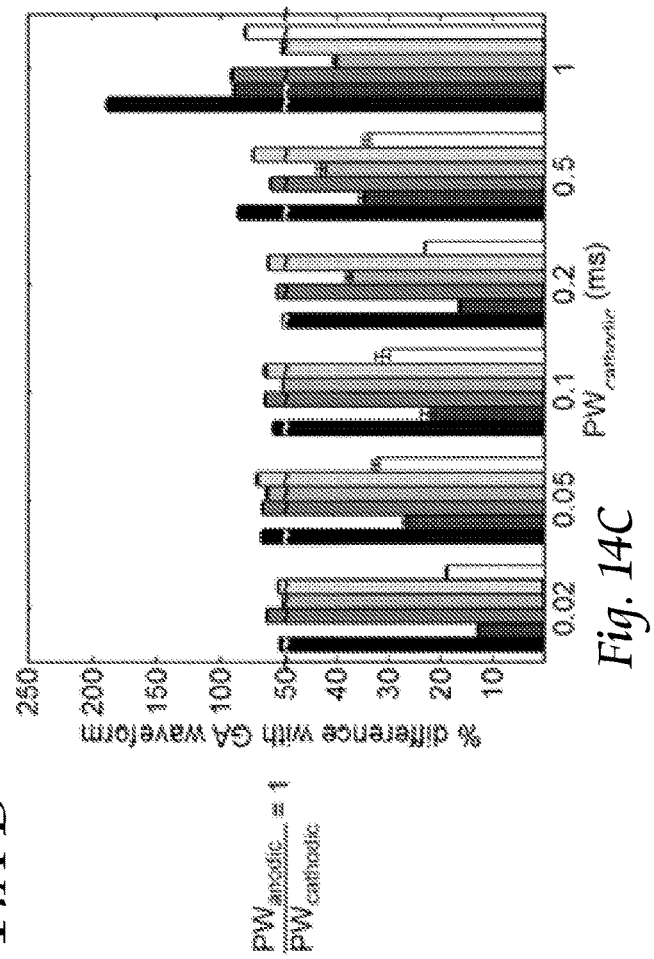
Figs. 14A-D

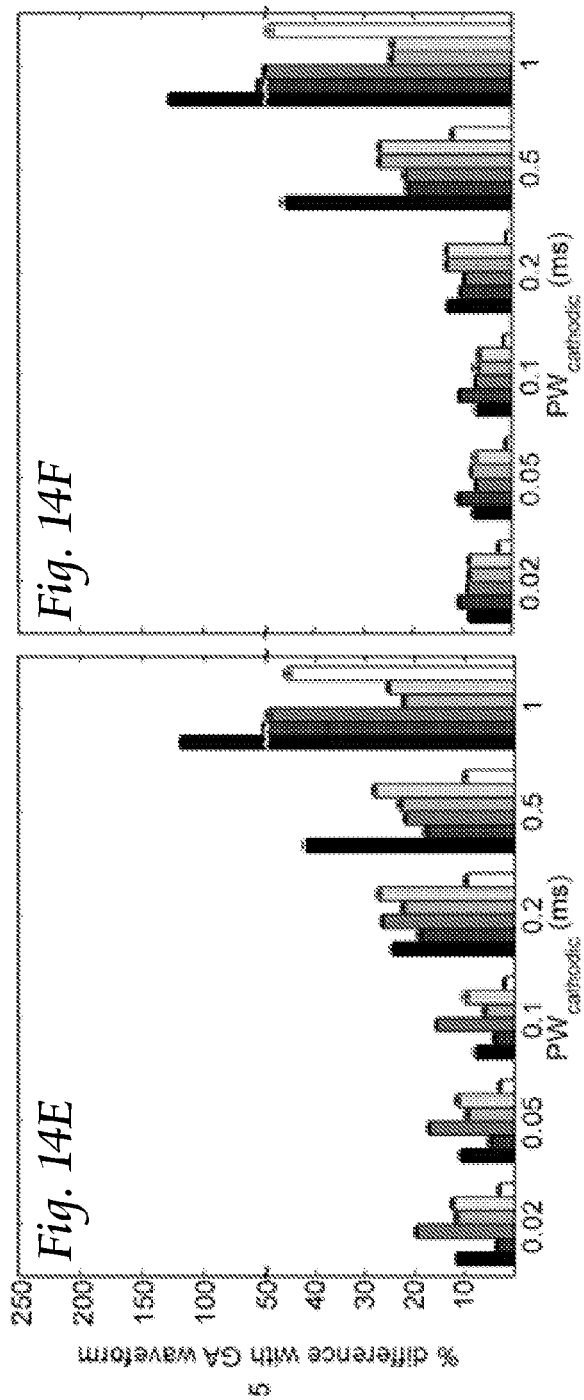
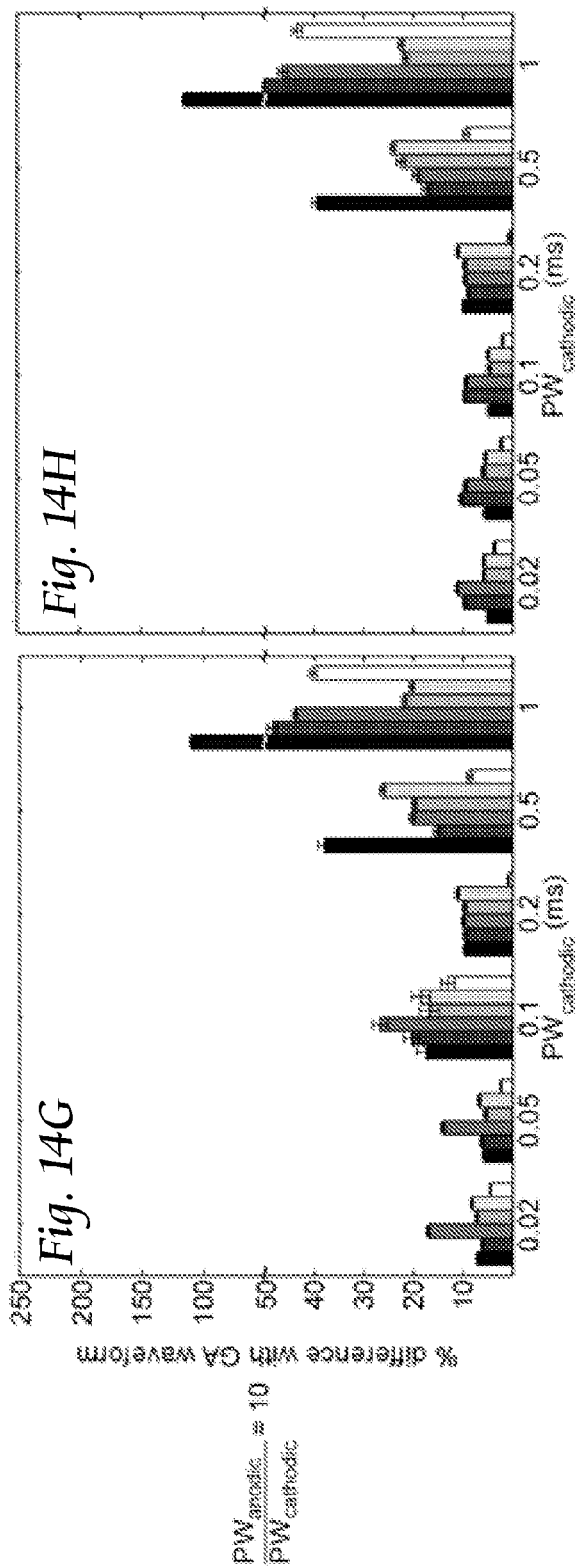
Figs. 14E-H

SYSTEM FOR GENERATING AND APPLYING WAVEFORM SHAPES FOR TREATING NEUROLOGICAL DISORDERS OPTIMIZED FOR ENERGY EFFICIENCY

CROSS-REFERENCE TO RELATED APPLICATIONS

This application is a continuation of U.S. patent application Ser. No. 14/796,216, filed on Jul. 10, 2015, now U.S. Pat. No. 9,707,397, entitled "Waveform Shapes for Treating Neurological Disorders Optimized for Energy Efficiency," which is a continuation of Ser. No. 13/118,081, filed May 27, 2011, entitled "Waveform Shapes for Treating Neurological Disorders Optimized for Energy Efficiency," which is now U.S. Pat. No. 9,089,708, which claims the benefit of U.S. Provisional Patent Application Ser. No. 61/348,963, Filed May 27, 2010, and entitled "Energy-Optimal Biphasic Waveform Shapes for Neural Stimulation," which are all incorporated herein by reference.

GOVERNMENT LICENSING RIGHTS

This invention was made in part With government support under NIH Grant Nos. R01 NS040894 and R21 NS054048. The government has certain rights to the invention.

FIELD OF THE INVENTION

This invention relates to systems and methods for stimulating nerves in mammals and, in particular, humans.

BACKGROUND OF THE INVENTION

Implantable and external electrical stimulators assist thousands of individuals with neurological disorders. These stimulators generate electrical Waveforms, Which are delivered by leads to targeted tissue regions to treat the neurological disorders. Examples of treating neurological disorders using electrical stimulation include deep brain stimulation, cortical stimulation, vagus nerve stimulation, sacral nerve stimulation, spinal cord stimulation, and cardiac pace makers and defibrillators.

Implantable stimulators are powered by either primary cell or rechargeable batteries. When the energy of a primary cell battery is depleted, the entire stimulator must be replaced through an expensive and invasive surgical procedure. The energy capacity of a rechargeable battery determines the recharge interval, as Well as the overall volume of the implant.

There are clinical benefits to reducing the frequency of battery-replacement surgeries or recharge intervals, as Well as reducing the physical size (volume) of the stimulator itself. The problem is how one alters stimulation parameters to achieve this objective without sacrificing clinical efficacy and generating unwanted side effects. For example, the energy efficiency of stimulation (i.e., how much energy is consumed for the generation of a given stimulation pulse) cannot be viewed in isolation. The charge efficiency of stimulation is also an important consideration with implanted devices. The charge delivered during a stimulus pulse contributes to the risk of tissue damage (Yuen et al. 1981; McCreery et al. 1990). If energy-efficient stimulation parameters deliver excessive amounts of charge, then the benefits of high energy efficiency are diminished.

As shown in FIGS. 1A and 1B, the energy efficiency of stimulation parameters is dependent upon the amplitude of the stimulation pulse (typically expressed, e.g., in a range from 10 μA upwards to 10 mA); the width or duration of the stimulation pulse (typically expressed, e.g., in a range from 20 μs upwards to 500 μs); the frequency of the pulses applied over time (typically expressed, e.g., in a range from 10 Hz upwards to 200 Hz); and the shape or waveform of the pulse (e.g., typically, depending upon the therapeutic objective, square (rectangular) (see FIG. 2A), or rising ramp (see FIG. 2B), or sinusoid (see FIG. 2C), or decreasing exponential (see FIG. 2D), or rising exponential (see FIG. 2E)).

Previous studies have used passive membrane models to analyze the effects of waveform shape on efficiency. All previous studies using passive membrane models have concluded that the energy-optimal waveform shape is a rising exponential (Offner 1946; Fishler 2000; Kajimoto et al. 2004; Jezernik and Moran 2005).

However, in more realistic models and in vivo experiments, the inventors have found that the rising exponential waveform proved to be no more energy-efficient than rectangular, ramp, or decaying exponential waveforms. In fact, in realistic membrane models, the inventors have found that energy-optimal Waveform shapes cannot be determined analytically because of the complexity and non-linearity of the equations that define the excitable membrane in the model. Also, a "brute force" method of testing every possible waveform shape is not feasible since the number of possible waveform shapes is infinite.

SUMMARY OF THE INVENTION

One aspect of the invention provides systems and methodologies that couple an optimization algorithm, such as a global optimization algorithm (e.g. a genetic algorithm) to a computational model of extracellular stimulation of a mammalian myelinated axon, to derive a set of stimulus wave forms that are optimized for a desired parameter, such as energy efficiency.

One aspect of the invention provides systems and methodologies that couple a genetic algorithm (GA) to a computational model of extracellular stimulation of a mammalian myelinated axon, to derive a set of stimulus wave forms that are optimized for energy efficiency. This aspect of the invention makes it possible in a systematic Way to generate and analytically validate energy-optimal waveform shapes.

Another aspect of the invention provides systems and methodologies that include a set of stimulation waveforms that are optimized using a specially configured genetic algorithm (GA) to be more energy-efficient than conventional waveforms used in neural stimulation, as well as more energy-efficient than the conventional waveforms for excitation of nerve fibers in vivo. The optimized GA waveforms are also charge-efficient.

The optimized energy-efficiency of the stimulation waveforms derived according to the invention make it possible to prolong battery life of stimulators, thus reducing the frequency of recharge intervals, the costs and risks of battery replacement surgeries, and the volume of implantable stimulators.

The set of stimulus waveforms optimized according to the invention for energy efficiency can be readily applied to deep brain stimulation, to treat a variety of neurological disorders, such as Parkinson's disease, movement disorders, epilepsy, and psychiatric disorders such as obsessive-compulsion disorder and depression, and other indications, such as tinnitus. The set of stimulus Waveforms optimized according to the invention for energy efficiency can also be readily applied to other classes of electrical stimulation of the nervous system including, but not limited to, cortical stimulation, and spinal cord stimulation, to provide the attendant benefits described above and to treat diseases or indications such as but not limited to Parkinson's Disease, Essential Tremor, Movement Disorders, Dystonia, Epilepsy, Pain, Tinnitus, psychiatric disorders such as Obsessive Compulsive Disorder, Depression, and Tourette's Syndrome.

BRIEF DESCRIPTION OF THE DRAWINGS

FIGS. 4A to 4C are How charts diagrammatically showing the operation of the genetic algorithm (GA) coupled to the computational model of extracellular stimulation of a mammalian myelinated axon.

FIGS. 6A and 6B illustrate the progression of the genetic algorithm (GA) coupled to the computational model of extracellular stimulation of a mammalian myelinated axon for a single trial (stimulation pulse Width (PW)=0.5 ms), FIG. 6A being a sequence of plots showing changes in waveform shapes across generations and the most energy-efficient waveform at each indicated generation, and FIG. 6B being a graph showing the minimum and mean energy of population across 10,000 generations, as convergence toward a common optimal energy-efficiency value occurs.

FIGS. 10A, 10B, and 10C are sensitivity plots for the GA waveforms to model parameters, FIG. 10A showing sensitivity to fiber diameter (D) (curves represent mean of the GA waveforms across 5 trials for PW=0.1 ms), and FIGS. 10B and 10C showing sensitivity to the Hodgkin-Huxley model (skewed Gaussian curves resulted) (curves represent the means of the resulting waveforms across 5 independent trials, and the gray regions define 95% confidence intervals for PW=0.2 ms (b) and PW=0.02 ms (c)) (amplitudes are not to scale). Additionally, the GA waveforms were shown to be insensitive to the number of Waveforms per generation population, the number of surviving waveforms per generation, the average initial amplitude of the waveforms, and the mutation rate. The GA waveforms were shown to be sensitive to changes in dt (smaller dt leads to more energy-efficient for short PW, and less energy-efficient for long PW).

14A to 14H show the energy efficiency of biphasic GA waveforms in a model of extracellular stimulation of a population of myelinated axons, FIGS. 14A and 14B being energy-duration curves for activation of 50% of the axons (mean+/−SE; n=5 different random populations of 100 axons), FIGS. 14C to 14H being energy efficiency of GA waveforms compared to conventional waveform shapes used in neural stimulation (mean+/−SE, n=5) (positive values of "% difference with GA waveform" indicate that GA waveforms were more energy-efficient), the Figures showing that waveforms with cathodic phase first were more energy-efficient than waveforms with anodic phase first for $PW_{cathodic} \leq 0.2$ ms, 0.05 ms, and 0.05 ms for $PW_{anodic}/PW_{cathodic}=1$, 5, and 10, respectively (Fisher's protected least significant difference (FPLSD): p<0.0001); however, waveforms with anodic phase first were more efficient for $PW_{cathodic} \geq 0.5$ ms and 0.2 for $PW_{anodic}/PW_{cathodic}=1$ and 5, respectively, and for $0.1 \text{ ms} \leq PW_{cathodic} \leq 0.5$ ms for $PW_{anodic}/PW_{cathodic}=10$ (FPLSD: p<0.0001); and energy efficiency improved as $PW_{anodic}/PW_{cathodic}$ increased (FPLSD: p<0.0001). FIGS. 14A to 14H show that, compared to the monophasic GA waveforms, the biphasic GA waveforms were less energy-efficient, but the difference in energy efficiency decreased as $PW_{cathodic}$ increased.

DESCRIPTION OF THE PREFERRED EMBODIMENTS

I. System Overview

Figure 1A:
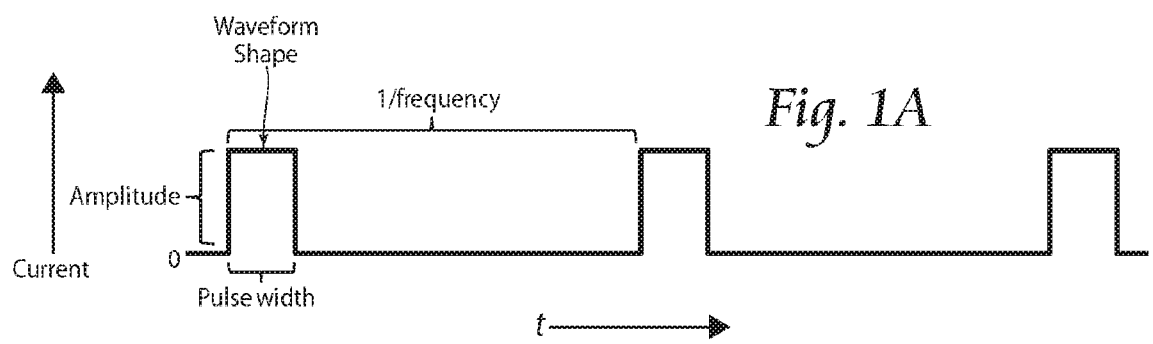
FIG. 1A is a first diagrammatic view (amplitude vs. time) of a stimulation waveform indicating stimulation parameters of a hypothetical neural stimulation train.
Figure 1B:
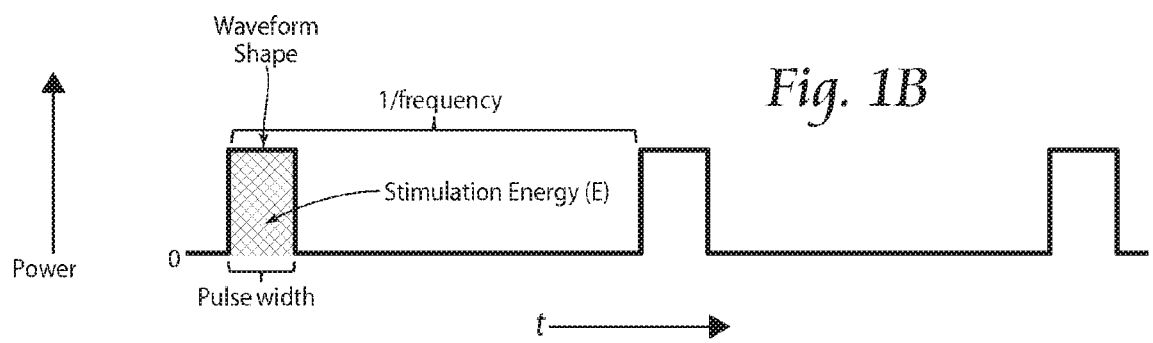
FIG. 1B is a second diagrammatic view (power vs. time) of a stimulation waveform indicating stimulation parameters of a hypothetical neural stimulation train.
Figure 2A:
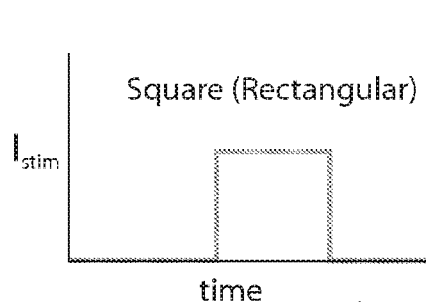
FIGS. 2A to 2E are diagrammatic views of typical waveforms used for neural stimulation.
Figure 2B:
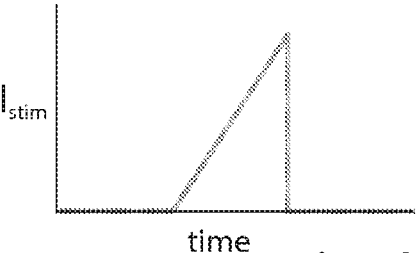
Figure 2C:
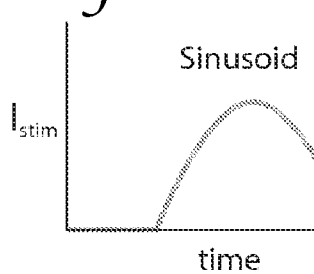
Figure 2D:
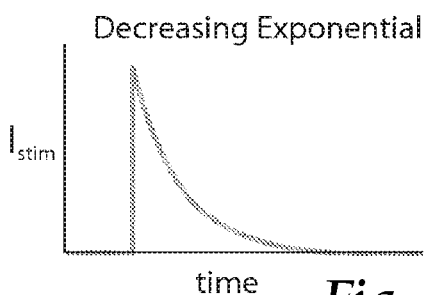
Figure 2E:
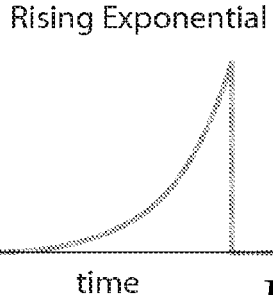
Figure 3:
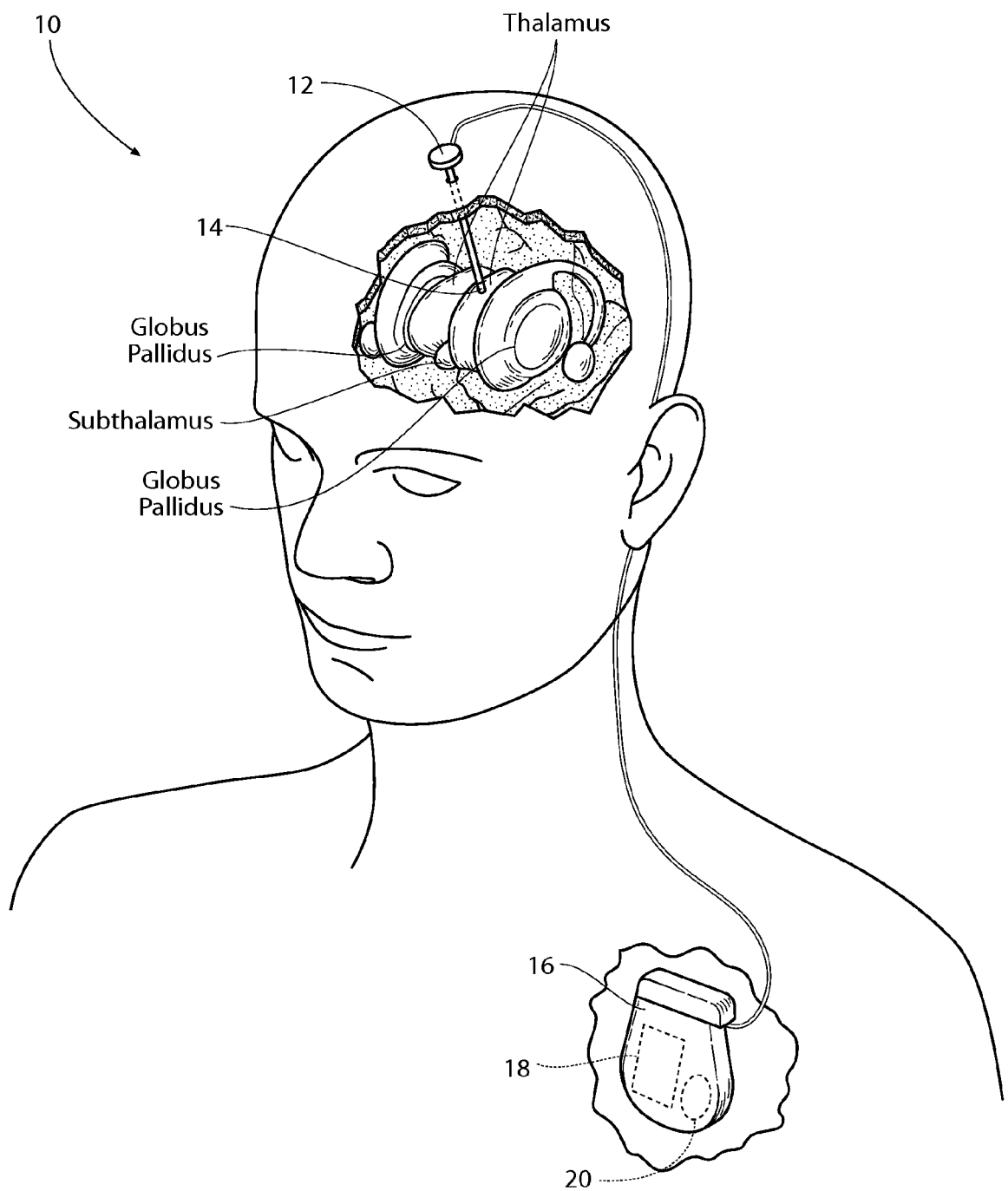
FIG. 3 is an anatomic view of a system for stimulating tissue of the central nervous system that includes a lead implanted in brain tissue coupled to a pulse generator that is programmed With stimulation parameters to provide a stimulus waveform that has been optimized for energy efficiency by coupling a genetic algorithm (GA) to a computational model of extracellular stimulation of a mammalian myelinated axon.

FIG. 3 is a system 10 for stimulating tissue of the central nervous system. The system includes a lead 12 placed in a desired position in contact With central nervous system tissue. In the illustrated embodiment, the lead 12 is implanted in a region of the brain, such as the thalamus, subthalamus, or globus pallidus for the purpose of deep brain stimulation. However, it should be understood, the lead 12 could be implanted in, on, or near the spinal cord; or in, on, or near a peripheral nerve (sensory or motor), in any subcutaneous tissue such as muscle tissue (including cardiac tissue) or adipose tissue for the purpose of selective stimulation to achieve a therapeutic purpose. In addition, the lead 12 may be utilized for transcutaneous stimulation Where electrodes are placed, not subcutaneous, but on an outer skin surface.

The distal end of the lead 12 carries one or more electrodes 14 to apply electrical pulses to the targeted tissue region. The electrical pulses are supplied by a pulse generator 16 coupled to the lead 12.

In the illustrated embodiment, the pulse generator 16 is implanted in a suitable location remote from the lead 12, e. g., in the shoulder region. It should be appreciated, however, that the pulse generator 16 could be placed in other regions of the body or externally to the body.

When implanted, at least a portion of the case or housing of the pulse generator can serve as a reference or return electrode. Alternatively, the lead 12 can include a reference or return electrode (comprising a bi-polar arrangement), or a separate reference or return electrode can be implanted or attached elsewhere on the body (comprising a mono-polar arrangement).

The pulse generator 16 includes stimulation generation circuitry, which preferably includes an on-board, programmable microprocessor 18, Which has access to and/or carries embedded code. The code expresses pre-programmed rules or algorithms under which desired electrical stimulation is generated, having desirable electrical stimulation parameters that may also be calculated by the microprocessor 18, and distributed to the electrode(s) 14 on the lead 12. According to these programmed rules, the pulse generator 16 directs the stimulation through the lead 12 to the electrode(s) 14, which serve to selectively stimulate the targeted tissue region. The code may be programmed, altered or selected by a clinician to achieve the particular physiologic response desired. Additionally or alternatively to the microprocessor 18, stimulation generation circuitry may include discrete electrical components operative to generate electrical stimulation having desirable stimulation parameters. As shown in FIG. 2, the stimulation parameters may include a pulse amplitude (expressed, e.g., in a range from 10 µA upwards to 10 mA); a pulse Width (PW) or duration (expressed, e.g., in a range from 20 µs upwards to 500 µs); a frequency of stimulation pulses applied over time (expressed, e.g., in a range from 10 Hz upwards to 200 Hz); and a shape or Waveform of the stimulation pulses. One or more of the parameters may be prescribed or predetermined as associated with a particular treatment regime or indication.

In the illustrated embodiment, an on-board battery 20 supplies power to the microprocessor 18 and related circuitry. Currently, batteries 20 must be replaced every 1 to 9 years, depending on the stimulation parameters needed to treat a disorder. When the battery life ends, the replacement of batteries requires another invasive surgical procedure to gain access to the implanted pulse generator. As will be described, the system 10 makes possible, among its several benefits, an increase in battery life.

As will be described in greater detail later, the stimulation parameters, which may be prescribed, used by the pulse generator differ from conventional stimulation parameters, which may be prescribed, in that the waveform shape of the pulses has been optimized by use of an optimization algorithm, such as a global optimization algorithm. An example of a global optimization algorithm used to optimize an electrical stimulation waveform is a genetic algorithm (GA) used to optimize energy efficiency of a waveform for neural stimulation. Use of the Waveform shapes optimized for energy-efficiency leads to a decrease in power consumption, thereby prolonging battery life, reducing battery size requirements, and/or reducing frequency of battery replenishment.

Although the following description is based largely on a genetic algorithm, other optimization algorithms may be employed in a computational model of neural stimulation to optimize the stimulation based on a cost function, which can include a variety of factors, such as energy efficiency. Other optimization algorithms that may be used include, for example, simulated annealing, Monte-Carlo methods, other evolutionary algorithms, swarm algorithms (e.g. ant colony optimization, bees optimization, particle swarm), differential evolution, firefly algorithm, invasive weed optimization, harmony search algorithm, and/or intelligent water drops.

II. Energy-Optimal Waveforms (Monophasic)

A. Overview

The inventors have implemented a genetic algorithm in a computational model of peripheral nerve stimulation, to determine the energy-optimal waveform shape for neural stimulation. The energy efficiencies of the GA waveforms were compared to those of conventional waveform shapes in a computational model of a population of axons as well as during in vivo stimulation of peripheral nerve fibers.

B. Deriving the Genetic Algorithms

1. Generally

The genetic algorithm seeks an optimal solution through a process based on the principles of biological evolution. As shown in FIG. 4A, the first generation of a GA starts with a population of candidate solutions. In FIG. 4A, there are two candidate stimulation parameters, each having a different wave form (rising ramp and square). The candidate solutions are analogous to natural organisms, and the stimulation parameters that characterize each candidate are its "genes".

Next, as further shown in FIG. 4A, the fitness of each solution is assessed using a cost function specific to the optimization problem. As will be described in greater detail later, the fitness is assessed in a computational model of extracellular stimulation of a single myelinated mammalian peripheral axon. The fitness of each candidate (n) is expressed in terms of energy efficiency ($Energy_n$).

As shown in FIG. 4B, the candidate solutions "mate" with each other, resulting in offspring solutions that possess a combination of the parents' genes (i.e., stimulation parameters), as well as, in time, the genes of the offspring that have mutated (a different stimulation parameter value, preferably not found in the parents). The fitness of both the mating process and mutations promote a thorough search of the solution space, to improve the chances of discovering the global optimum rather than a local optimum. Following each generation, the population is partially or completely replaced by the offspring. As the GA progresses, beneficial genes remain in the gene pool of the population While unfavorable genes are discarded.

Figure 4C:
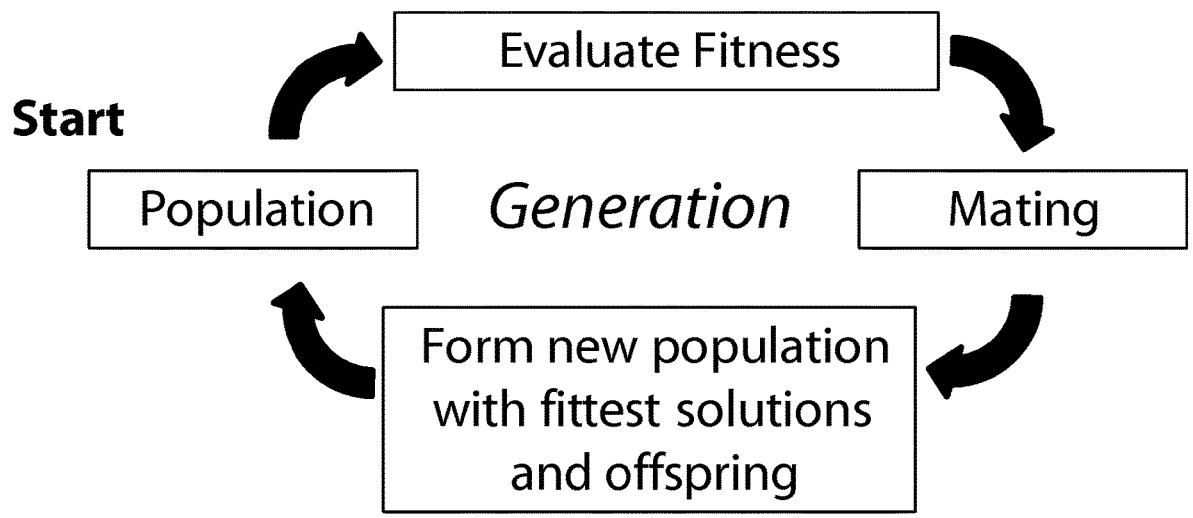

As shown in FIG. 4C, this process—evaluating fitness, mating, and replacing solutions is repeated either for a predetermined number of generations (such as 10, 20, 50, 100, 200, 500, 1000, 2000, 5000, 10,000, or more generations) or until the solutions converge upon, towards, or within a desirable range from a fitness value. The solution with the overall greatest fitness is the resulting estimate of the optimal solution.

2. The Specific Genetic Algorithm

Figure 5A:
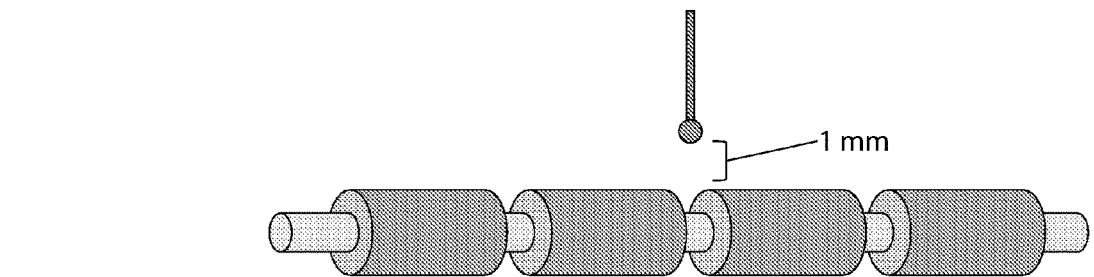
FIGS. 5A and 5B are diagrammatic views of the computational model of extracellular stimulation of a mammalian myelinated axon, which is coupled to the genetic algorithm (GA).
Figure 5A:
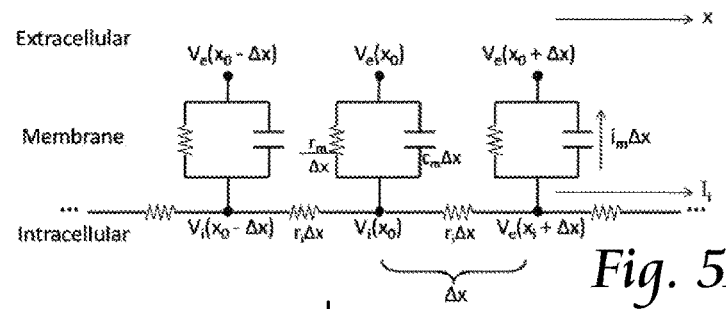
Figure 5B:
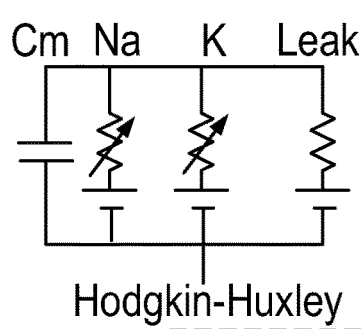
Figure 5B:
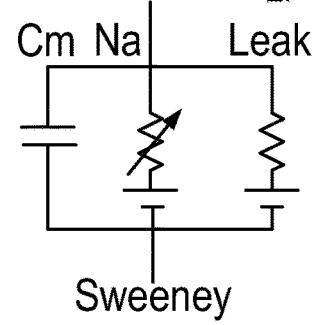
Figure 5B:
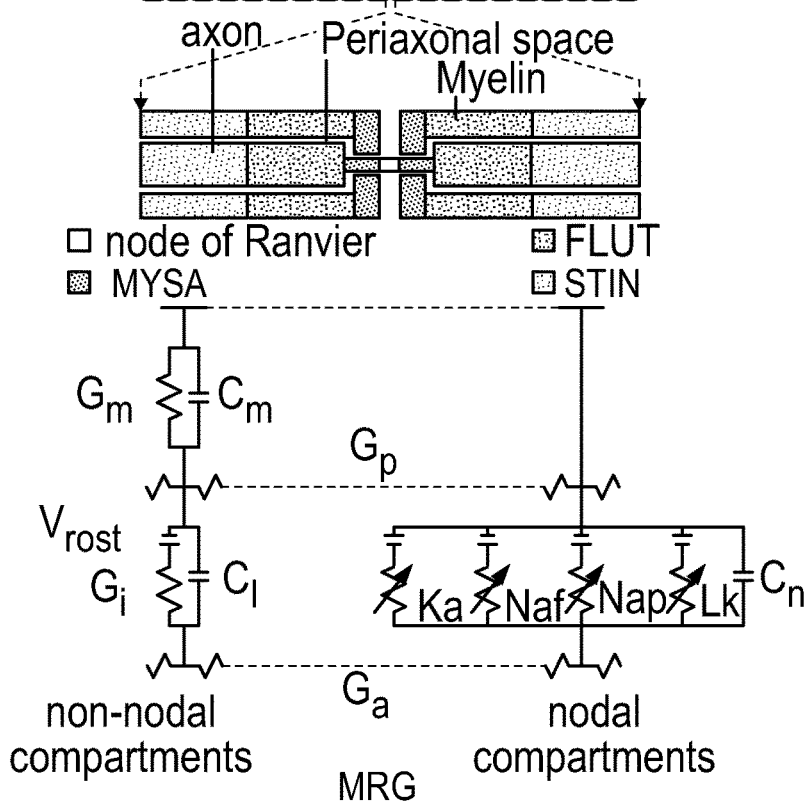

A specific generic algorithm (GA) was derived to seek the energy-optimal waveform shape in a computational model of extracellular stimulation of a single myelinated mammalian peripheral axon, which is shown in FIGS. 5A and 5B.

Simulations were run in NEURON (Hines and Carnevale 1997) using the MRG model (fiber diameter=11.5 μm), Which represented a myelinated mammalian peripheral axon as a double cable model with a finite impedance myelin sheath and explicit representation of the nodes of Ranvier, paranodal sections, and internodal segments (McIntyre et al. 2002) (see FIG. 5B). Stimulation was delivered through a current-regulated point source situated within a conductive medium (300 Ω-cm) (McNeal 1976) located 1 mm directly above the center node of the fiber (see FIG. 5A).

C. Deriving the GA Waveforms

FIG. 6A shows an overview of the results of the GA waveform derivation process.

For each generation of the GA, the population consisted of fifty (50) stimulation waveforms with fixed pulse width (PW). Waveforms were discretized in time using a time step equal to that of the computational model (dt=0.002 ms), and the genes of each waveform represented the amplitudes at every time step. The values of the genes of the waveforms of the first generation were selected at random from a uniform distribution between zero and two times the cathodic threshold of stimulation with a rectangular waveform at the equivalent PW (e.g., 807 μA for PW=10 μs; 190 μA for PW=100 μs; 79.8 μA for PW=1 ms).

The cost function (F) used to evaluate the fitness of each waveform equaled the sum of the energy consumed by the waveform (E) and a substantial penalty if the waveform failed to elicit an action potential:

$$F = E + \text{Penalty} \qquad \text{Equation (1)}$$

$$E = \int_0^{PW} P(t)dt \propto dt * \sum_{n=1}^{N} I_n^2 \qquad \text{Equation (2)}$$

Where P is instantaneous power, t is time, I is the instantaneous current, and N is the number of discretizations (genes) of a stimulation waveform. If the waveform elicited an action potential, then Penalty equaled 0, but if the waveform did not elicit an action potential, then Penalty equaled 1 nJ/ohm (2 to 3 orders of magnitude larger than E).

At the end of each generation, the top ten (10) fittest waveforms (i.e., smallest F) remained in the population while the remaining forty (40) waveforms were replaced by offspring. Every waveform, regardless of its value of F, had an equal probability of being selected as a parent, and each offspring was generated by combining the genes of two parents using two crossover points. A crossover point was a randomly selected gene location, where during mating the genes prior to the crossover point from one parent were combined with the genes beyond the crossover point from the other parent. With two crossover points, the effect was a swap of a segment of one parent's genes with the corresponding section of the other parent's genes.

Each gene of the offspring was mutated by scaling the value by a random factor chosen from a normal distribution (μ=1, ρ2=0.025). Because the initial waveforms were monophasic cathodic pulses, the genes were restricted to negative values.

The GA was run using a wide range of PWs (0.02, 0.05, 0.1, 0.2, 0.5, 1, and 2 ms) to determine whether the outcome of the GA varied with PW. For each PW, the GA was run for 5 independent trials of 10,000 generations with different initial populations. For each trial, the following was recorded: the energy consumed by the most energy-efficient waveform of each generation (generation energy); the most energy-efficient waveform of the final generation (GA waveform); and the charge (Q) delivered by the GA waveform, where:

$$Q = \int_0^{PW} I(t)dt = dt * \sum_{n=1}^{N} I_n. \qquad \text{Equation (3)}$$

For each PW, the means and standard errors of the energy and charge consumed by the GA waveforms across the 5 independent trials were recorded.

In this particular GA, the only considerations for the cost function (F) were energy efficiency and whether or not an action potential was elicited in the axon. However, F can use other measures besides energy efficiency, either as the sole consideration of F, or in combination with other measures. These other measures may include charge efficiency, power efficiency (i.e., peak power of waveform), maximum voltage or current, therapeutic benefit of stimulation, adverse effects, and selectivity of stimulation (i.e., activation of one population of neurons or fibers defined by location, size, or type without activation of other populations). F may include different weights associated with each measure, reflecting the relative importance of each measure. For example, F may consider both energy and charge, and energy may be three times as important as charge for a given application of stimulation. Then, F=0.75 E+0.25 Q. Thus, the methodology according to the present invention may produce waveform shapes that may be optimized to any particular cost function, including desired cost parameters.

D. The Resulting GA Waveforms

Figure 7:
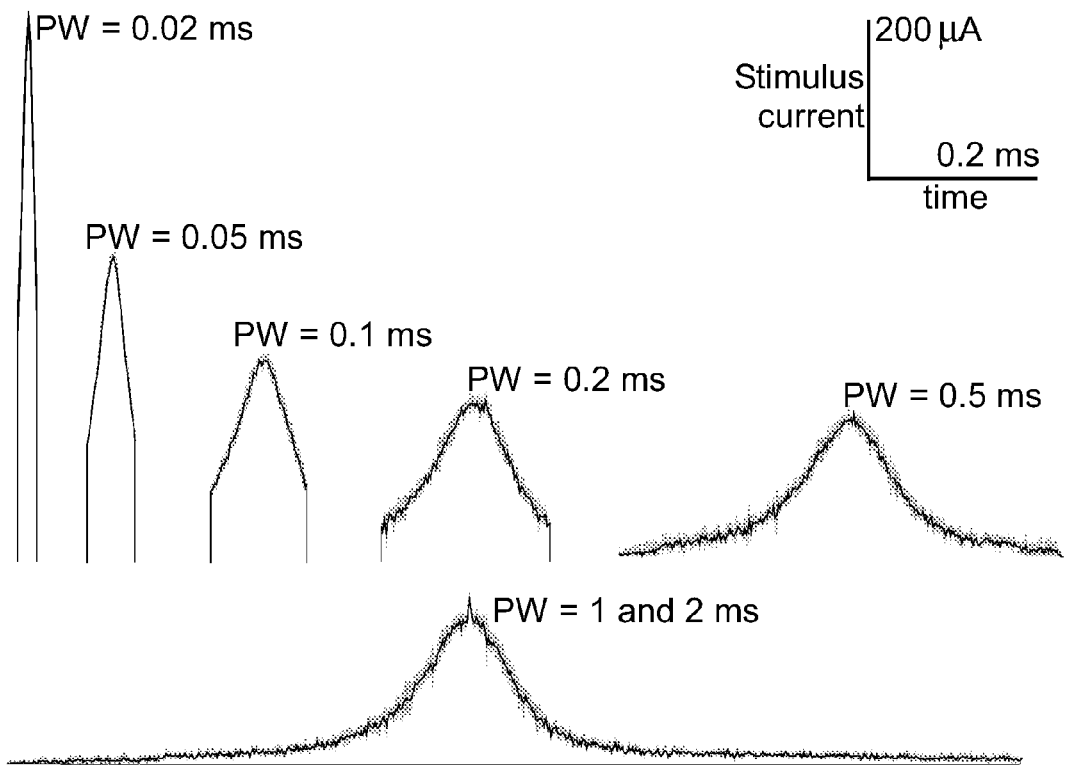
FIG. 7 shows curves of the energy-optimal stimulation waveforms resulting from the GA coupled to the computational model of extracellular stimulation of a mammalian myelinated axon, for different PWs, the curves representing the means of the resulting waveforms across five independent trials, and the gray regions defining 95% confidence intervals, the waveforms for PW=1 and 2 ms being combined, and the leading and trailing tails of low amplitude were truncated.

Each trial of the GA began with a different population of random waveforms, but by the end of each trial, the GA converged upon consistent and highly energy-efficient waveform shapes (as FIGS. 6A and 6B show). The generation energy converged to within 1% of the final generation energy by 5000 generations for PW≤0.5 ms and by 9000 generations for PW=1 and 2 ms. As FIG. 7 shows, for each PW, the GA waveforms were very similar across trials, and across PWs the shapes of the GA waveforms were quite similar. As FIG. 6 shows, for PW≤0.2 ms, the GA waveforms resembled truncated Gaussian curves, with the peak near the middle of the pulse. For PW≥0.5 ms, the shapes of the GA waveforms also resembled Gaussian curves but with leading and/or trailing tails of negligible amplitude.

E. Assessing the Energy-Efficiency of GA Waveforms

1. The Population Model (i) Methodology

Figure 8:
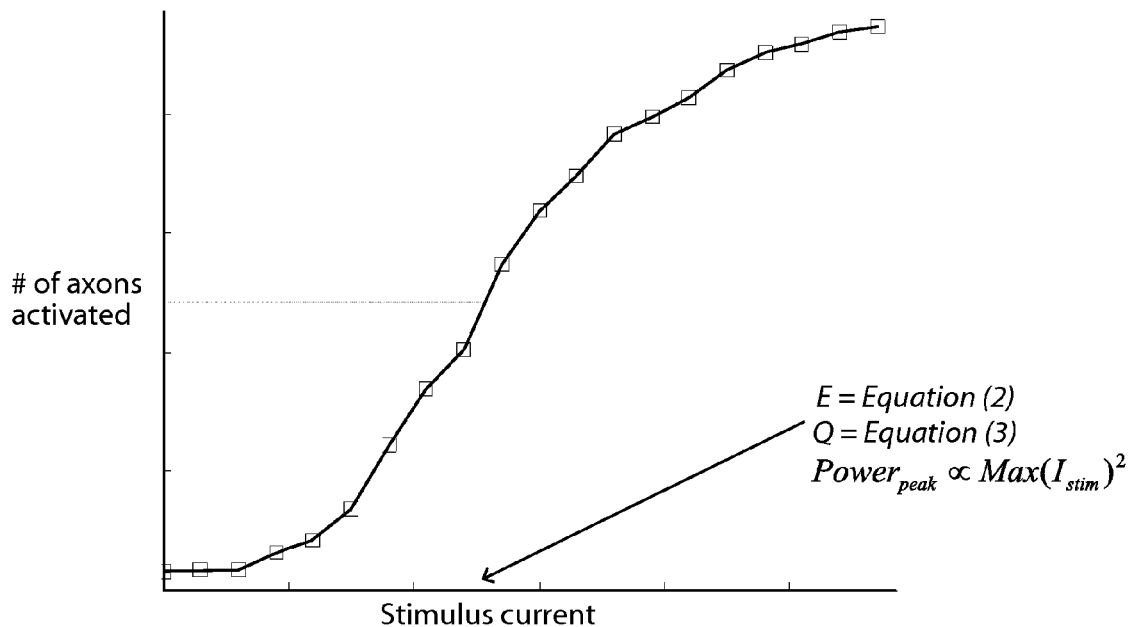
FIG. 8 is a representative input/output (I/O) curve that was constructed when evaluating the energy-efficiency of the GA waveforms in a population model of one hundred (100) parallel MRG axons (11.5-μm diameter) distributed uniformly Within a cylinder With 3-mm diameter.

The GA waveforms were evaluated in a population model of one hundred (100) parallel MRG axons (11.5-μm diameter) distributed uniformly within a cylinder with a 3-mm diameter. Extracellular stimulation was delivered through a point current source located at the center of the cylinder. For each PW (0.02, 0.05, 0.1, 0.2, 0.5, 1, and 2 ms), ten (10) populations of randomly-positioned axons were selected. For each population, input/output (I/O) curves (see FIG. 8) were constructed of the number of fibers activated vs. E, as well as the number of fibers activated vs. Q. To adjust the stimulation amplitude of a waveform, the entire waveform was scaled. For each I/O curve, the E and Q needed to activate 50% of the entire population were computed, and the means and standard errors of these values across the ten (10) axon populations were calculated. Using the same axon populations, I/O curves for conventional waveforms used in neural stimulation were calculated: rectangular, rising/decreasing ramp, rising/decaying exponential, and sinusoid waveforms (See Appendix for the equations for the conventional waveforms).

(ii) Results (a) Overview

Figure 9A:
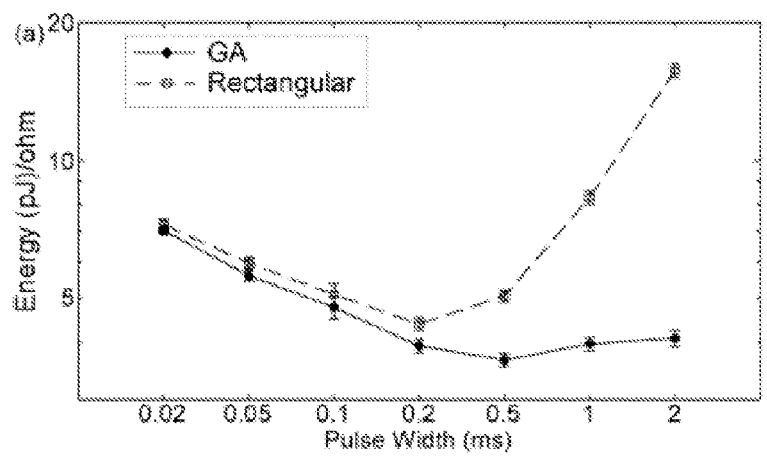
FIGS. 9A to 9C are plots showing the energy efficiency of the GA waveforms in a model of extracellular stimulation of a population of myelinated axons, FIG. 9A showing the energy-duration curves for activation of 500 of the axons (mean+/−SE; n=10 different random populations of 100 axons), FIG. 9B showing the energy efficiency of the GA waveforms compared to conventional waveform shapes used in neural stimulation (mean, n=10; SE was negligible) (positive values of "% difference with GA waveform" indicate that the GA waveforms were more energy-efficient) and FIG. 9C showing the energy efficiency plotted against charge efficiency.
Figure 9B:
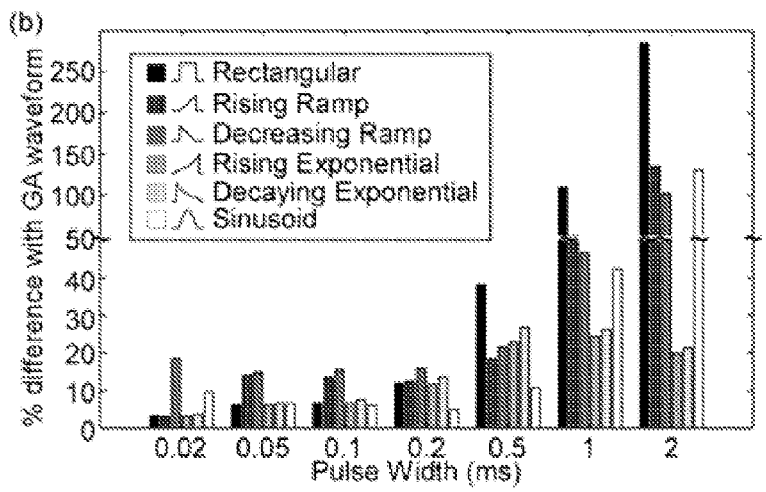

The GA waveforms were more energy-efficient than the conventional stimulation waveform shapes for all PWs in the population models. The energy-duration curve of the GA waveforms was concave up (see FIG. 9A), and the minimum E for the GA waveforms across PWs was less than the minimum E for the conventional waveform shapes. Of these other shapes, the shape that most resembled the GA waveforms—the sinusoid—had the lowest minimum energy across PWs. For PW≤0.2 ms, the GA waveforms were slightly more energy-efficient (<20%) than the other waveform shapes (see FIG. 9B). Between PW=0.2 ms and 0.5 ms, the differences in energy efficiency between GA waveforms and the conventional shapes increased considerably, and these differences increased further with PW for all but the exponential waveforms. Because the positions of the axons were randomized in the population model, these results demonstrate that the superior energy efficiency of the GA waveforms was independent of the location of the electrode with respect to the axon.

Figure 9C:
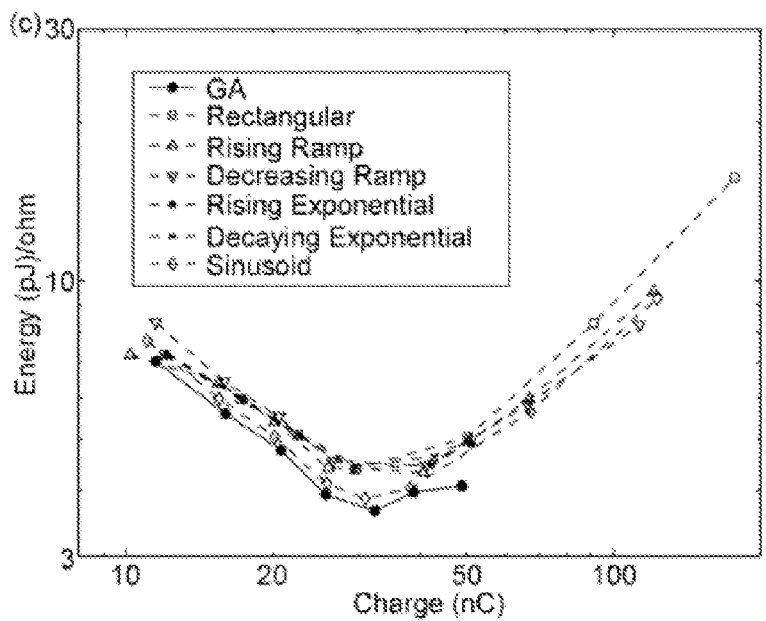

The GA waveforms were also more energy-efficient than most of the waveform shapes when energy was plotted against charge. For all waveform shapes, the curves of E vs. Q were concave up and many of the curves overlapped substantially (see FIG. 9C). However, the curves for the GA waveforms and sinusoid lay under the other curves, indicating that for a given amount of charge, the GA and sinusoid waveforms consumed less energy to reach threshold than the other waveform shapes.

(b) GA Waveform Sensitivity Analysis

As shown in FIG. 10A, the energy-optimal waveform shapes were largely insensitive to variations in the parameters of the GA. Doubling or halving the number of waveforms that survived to the next generation or the number of waveforms in each generation had no substantial effects on the shape of the GA waveforms or their energy efficiencies (<0.1% difference). Also, the amplitudes of the waveforms in the initial generation were scaled between 04-16 times the original amplitudes, and scaling factors>0.8 had little effect on the shape and energy efficiency (<0.1% difference) of the GA waveform. Scaling factors below 0.6, however, resulted in initial waveforms that were all below threshold, and the GA did not converge to an energy-efficient waveform. In addition, the variance of the normal distribution used in mutations was scaled between 0-4 times the original variance. With variance:0 (no mutations), the GA rapidly converged on an energy-inefficient waveform. However, for all other values of variance the GA produced nearly identical GA waveforms with approximately the same energy efficiencies (<0.4% difference).

As shown in FIG. 10B, although the shape of the GA waveforms remained consistent when dt was varied between 0.001-0.01 ms, the energy efficiency did change. Smaller values of dt produced finer resolution of the waveform shape, which created more energy-efficient GA waveforms for PW≤0.1 ms (|ΔE|<110). However, the improved resolution also led to less energy-efficient GA waveforms for PW≥1 ms, as a result of more noise in the waveform (|ΔE|<10.5%).

In addition to using a fiber diameter of 11.5 pm, we ran the GA with fiber diameters of 5.7 pm and 16 pm. The GA waveforms produced for each fiber diameter remained the most energy-efficient waveforms in their respective models, and their overall shapes were consistent across diameters (see FIG. 10A). Further, the GA waveforms optimized for diameter: 11.5 um (see FIG. 7) were still more energy-efficient than the conventional waveform shapes for excitation of the other two diameters.

The shape and efficiency of GA waveforms were dependent on the model of the neural membrane. We ran the GA in a model of a myelinated axon that consisted of nodes with Hodgkin-Huxley membrane parameters connected by electrically insulated myelinated internodes. This model differed from the MRG model both geometrically (e.g., no paranodal sections) and physiologically (e.g., lower temperature, no persistent sodium channels), but the fiber diameter and electrode-fiber distance were unchanged. In the Hodgkin-Huxley model, for PW≤0.05 ms the GA waveforms generated in the Hodgkin-Huxley model were still unimodal as in the MRG model but were asymmetric (see FIG. 10B). However, for PW=0.02 ms the GA waveforms from the two models diverged (see FIG. 10C). In addition, when tested in the Hodgkin-Huxley model, the original GA waveforms from the MRG model were not uniformly more energy-efficient than conventional waveform shapes.

(c) GA Waveform Fit With Analytical Equation

To gain a better understanding of the exact shapes of the energy-optimized waveforms, the GA waveforms were fitted to a piece-wise generalized normal distribution:

$$f(t) = A*e^{-\left(\frac{|t-\mu|}{\alpha_L}\right)^{\beta_L}} \text{ for } t \leq \mu$$
$$= A*e^{-\left(\frac{|t-\mu|}{\alpha_R}\right)^{\beta_R}} \text{ for } t > \mu.$$

Equation (4)

Where A is the amplitude at the peak, located at t=μ; α's and β's are scale and shape parameters, respectively, and must be greater than zero and the α's and β's are preferably less than infinity; and the subscripts correspond to the left (L) and to the right (R) of the peak. When αL=αR and βL=βR, the function is symmetric about β, and the values of β dictate the kurtosis (i.e., peakedness) of the waveform. When αL≠αR and/or βL≠βR, varying degrees of kurtosis and skewness can be produced [see Appendix for the equations]. Thus, Equation (4) may be used to produce an energy-optimal electrical stimulation waveform The parameters of Equation (4) were optimized to fit the mean GA waveforms (i.e., as shown FIG. 7) using the lsqcurvefit function in Matlab (R2007b; The Mathworks, Natick, Mass.). The least-square optimized waveforms fit well with the energy-optimized waveforms ($R2>0.96$). Across PWs, the fitted waveforms were not very skewed (−0.5<skewness<0.5, where skewness=0 is perfect symmetry), had sharper peaks (kurtosis>0.55) than the normal distribution (kurtosis=0), and the kurtosis of the fitted waveforms increased with PW.

A modified GA was also run, where the stimulation waveforms were characterized by Equation (4) instead of by the amplitudes at each time step. As a result, all waveforms were characterized by only six parameters—A, μ, αL, αR, βL, and βR—and initial values of these parameters were selected at random from uniform distributions (A: between zero and four times the cathodic threshold of stimulation with a rectangular waveform at equivalent PW; μ: 0–PW; α's: 0.01-0.5; β's: 0.01-3).

Preferably, a waveform defined at least in part by Equation (4) is generated or controlled by a microprocessor, which may accept various values for the indicated parameters. The peak current amplitude (A) varies with the stimulation application, and may vary between patients, but as described earlier, typically ranges from about 10 μA to about 10 mA. Parameter μ is preferably between zero (0) and the stimulation pulse width (PW). Parameters αL, αR, βL, and βR are preferably greater than 0 and less than infinity. One exemplary set of preferred alpha and beta values for a monophasic GA waveform is alpha values in the range of about 0.008 milliseconds to about 0.1 milliseconds and beta values in the range of about 0.8 to about 1.8. However, the alpha and beta values may well fall outside of this range under different circumstances, and changes in the values may be directly associated with a given fiber diameter.

The GA waveforms that resulted from optimization with this modified GA were not substantially different from the waveforms generated by the initial GA. The shapes of the waveforms were quite similar to the initial GA waveforms across all PWs (R2>0.93), and the energy efficiencies improved very little (<2%) for PW≤0.5 ms. However, the modified GA waveforms were more energy-efficient than the initial GA waveforms for PW=1 and 2 ms (5.6% and 10.4%, respectively), as a result of the smoothness of the modified GA waveforms and their ability to reach amplitudes near zero at the tails. Consequently, the energy-duration curve with this GA was not concave up as with the original GA, but instead, E remained constant as PW increased.

2. In Vivo Experiments
(i) Surgical Preparation

All animal care and experimental procedures were approved by the Institutional Animal Care and Use Committees of Duke University and were followed according to The Guide to the Care and Use of Laboratory Animals, 1996 Edition, National Research Council.

Experiments were performed on 3 adult male cats. Sedation was induced with acepromazine (Vedco Inc., 0.3 mg/kg; S.Q.), and anesthesia was induced with ketamine HCl (Ketaset 35 mg/kg; I.M.) and maintained during the experiment with α-chloralose (Sigma-Aldrich, Inc., initial 65 mg/kg supplemented at 15 mg/kg; I.V.). The cat was intubated, and respiration was controlled to maintain end tidal CO2 at 3-4%. Core temperature was monitored and maintained at 39° C. Fluid levels were maintained with saline solution and lactated ringers delivered through the cephalic vein (15 ml/kg/hr, I.V.). Blood pressure was monitored using a catheter inserted into the carotid artery.

Figure 11A:
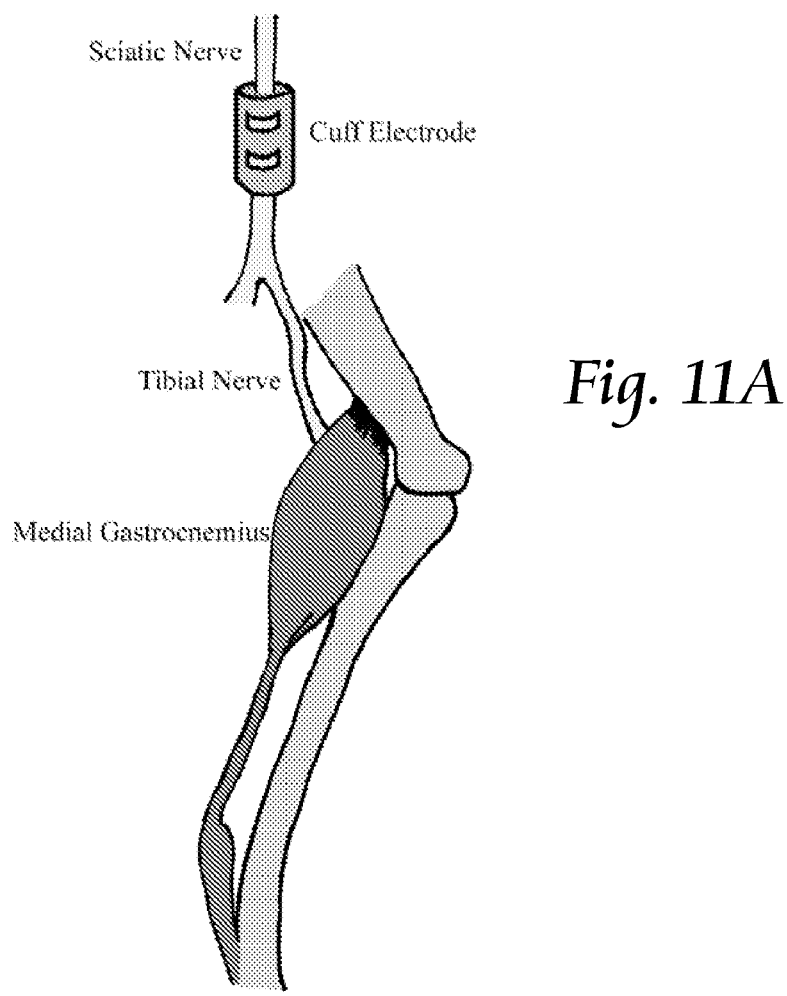
FIGS. 11A and 11B show the set up for the in vivo evaluation of the GA waveforms.
Figure 11B:
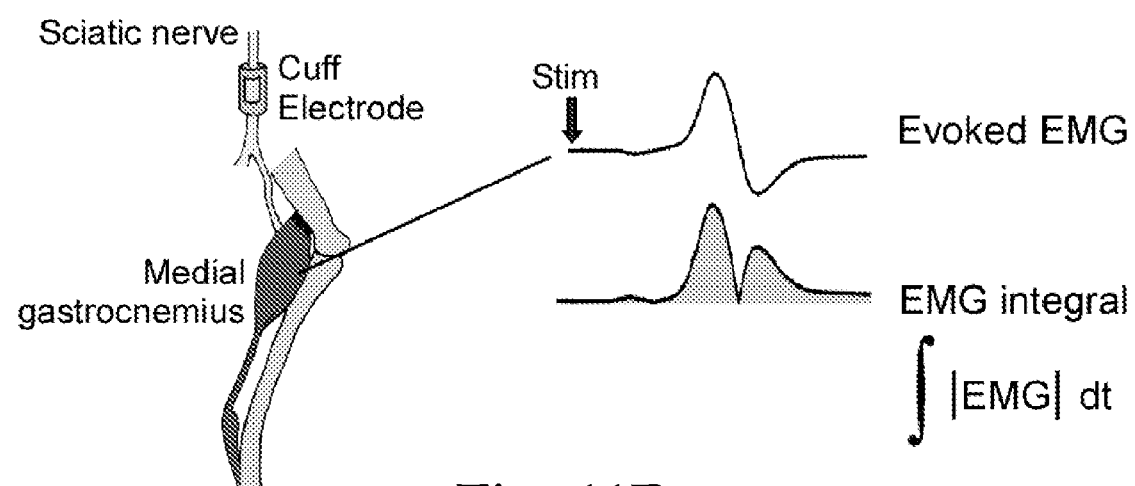

The sciatic nerve was accessed via an incision on the medial surface of the upper hindlimb. As FIG. 11A shows, a monopolar cuff electrode, composed of a platinum contact embedded in a silicone substrate, was placed around the nerve and secured with a suture around the outside of the electrode. The return electrode was a subcutaneous needle. Two stainless steel wire electrodes were inserted into the medial gastrocnemius muscle to measure the electromyogram (EMG) evoked by stimulation of the sciatic nerve (see FIG. 11B). The EMG signal was amplified, filtered (1-3000 Hz), recorded at 500 kHz, rectified, and integrated to quantify the response (EMG integral).

Stimulation and recording were controlled with Labview (DAQ: PCI-MIO-16E-1) (National Instruments, Austin, Tex.). A voltage waveform was delivered at a rate of 500 ksamples/s to a linear voltage-to-current converter (bp isolator, FHC, Bowdoin, Me.) and delivered through the cuff electrode. The voltage across (V) and current through (I) the cuff electrode and return electrode were amplified (SR560, Stanford Research Systems, Sunnyvale, Calif.) and recorded (fsample=500 kHz). The energy delivered during stimulation was determined by integrating the product of V(t) and I(t):

$$E=\int_0^{PW}P(t)dt=\int_0^{PW}V(t)I(t)dt \qquad \text{Equation (5)}$$

The charge delivered during stimulation was determined by integrating I(t) using Equation (3), above.

(ii) Recruitment Curves

Recruitment curves of the integral of the rectified EMG as a function of E and Q were measured for rectangular, decaying exponential (time constant [τ]=132, 263, and 526 μs), and GA waveforms at various PWs (0.02, 0.05, 0.1, 0.2, 0.5, and 1 ms) in random order. At frequent intervals over the course of the experiment, stimulation with the rectangular waveform at a fixed PW was provided to monitor shifts in threshold. Threshold shifts occurred in only one animal, and the values of E and Q were scaled accordingly. Recruitment curves were generated using a similar procedure as in the computational models: stimulus amplitude was incremented, three (3) stimulation pulses were delivered at −1 Hz at each increment, and the average values of E, Q, and EMG integral were recorded. From each recruitment curve, the values of E and Q required to generate 50% of the maximal EMG were calculated, and the values at PW=0.02 ms for the rectangular waveform were defined as baseline values. Subsequently, all values of E and Q were normalized to their respective baseline value, and the means and standard errors across experiments were calculated.

After log-transformation of the data, the effects of waveform shape on energy and charge efficiency were analyzed. A two-way repeated measures ANOVA was performed for each measure of efficiency; the dependent variable was E or Q, and the independent variables were waveform shape, PW (within-subjects factors), and cat (subject). Where interactions between waveform shape and PW were found to be significant (p<0.05), the data were subdivided by PW for one-way repeated measures ANOVA. Again, the dependent variable was E or Q, and the independent variables were waveform shape (within-subjects factor) and cat (subject). For tests which revealed significant differences among waveforms (p<0.05), post hoc comparisons were conducted using Fisher's protected least significant difference (FPLSD). Although data were log-transformed for statistical analysis, data were plotted as average percent difference with respect to the GA waveforms.

(iii) Results

Figure 12A:
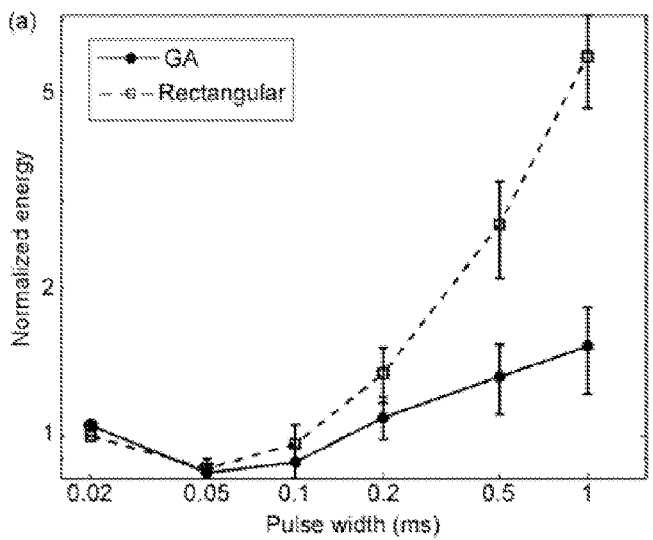
FIGS. 12A, 12B, and 12C show the in vivo measurements of energy efficiency of neural stimulation with the GA Waveforms, FIG. 12A showing the energy-duration curves for generation of 50% of maximal EMG (mean+/−SE; n=3), FIG. 12B showing the energy efficiency of GA waveforms compared to rectangular and decaying exponential waveforms (mean+/−SE; n=3) (positive values of "% difference with GA waveform" indicate that GA waveforms were more energy efficient), and FIG. 12C showing energy efficiency plotted against charge efficiency.
Figure 12B:
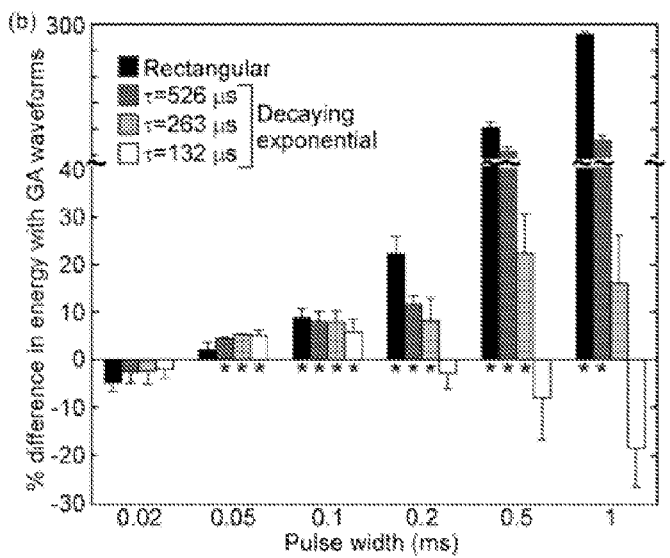
Figure 12C:
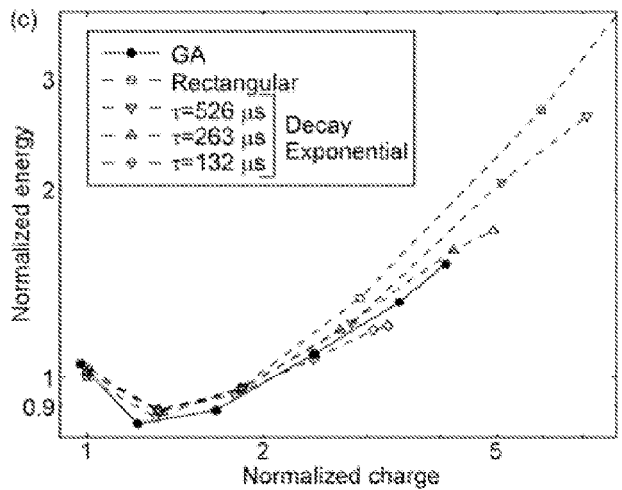

The in vivo measurements comparing the efficiency of GA waveforms to rectangular and decaying exponential waveforms largely corroborated the results of the population model. For PW 0.05 ms, the GA waveforms were significantly more energy-efficient than most of the rectangular and decaying exponential waveforms (p<0.05, FPLSD) (see FIGS. 12A and 12B). Although the decaying exponential with τ132 μs appeared to be more energy-efficient than the GA waveforms for PW≥0.5 ms, this result was misleading; for long PWs, increasing the PW for exponential waveforms simply extends the low-amplitude tail, which has negligible effects on excitation. As a result, the energy-duration curve for the exponential waveforms leveled off at long PWs, while the energy-duration curve for the GA waveforms increased with PW, as in the population model. When normalized E was plotted against normalized Q, the GA waveforms appeared to be more energy-efficient than the rectangular waveform for normalized Q>2 (see FIG. 12C). However, the GA waveforms were not substantially more energy-efficient than the decaying exponential waveforms.

III. Energy-Optimal Waveforms (Biphasic)

The original GA revealed energy-optimal waveforms for monophasic stimulation. However, most waveforms used for nerve stimulation are biphasic. Because the charge recovery pulse can influence the threshold of the primary pulse (van den Honert and Mortimer 1979), it was heretofore unclear whether the monophasic GA waveforms would remain energy-optimal for biphasic stimulation. First, thresholds were recalculated in the single fiber model for all waveform shapes with the addition of rectangular charge-balancing anodic phases. The duration was varied ($PW_{anodic}/PW_{cathodic}$=1, 5, or 10), as was the timing (preceding or following the cathodic phase) of the charge-balancing phase. Amplitudes of the anodic phases were adjusted to produce zero net charge for the entire waveform, and E was calculated from both phases of the waveform.

The biphasic results showed that the GA waveforms optimized for monophasic stimulation were not the most energy-efficient waveforms across all PWs. Therefore, the GA was modified to seek energy-optimal biphasic waveform shapes. For each combination of duration and timing (i.e., before or after the cathodic phase) of the rectangular charge-balancing anodic phase, five (5) separate trials were run of the GA to optimize the shape of the cathodic pulse for PW=0.02-1 ms, and E was calculated from both the anodic and cathodic phases of the waveform.

Figure 13:
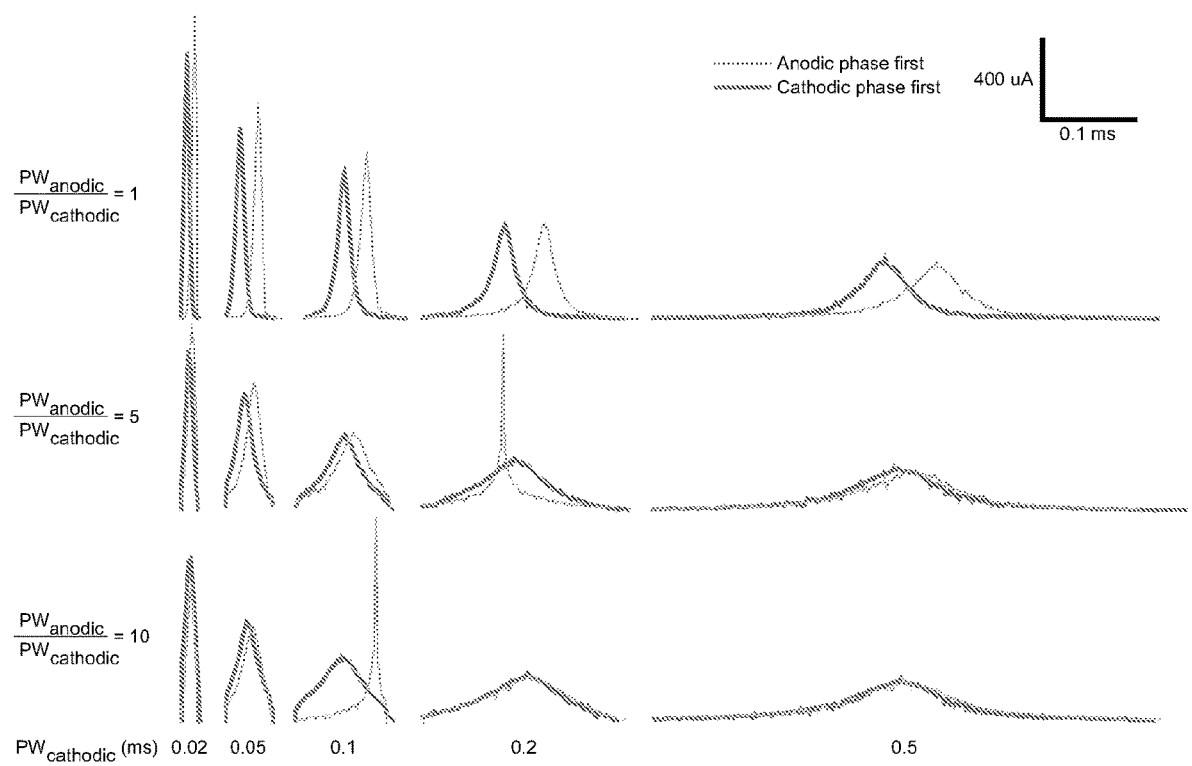
FIG. 13 shows the energy-optimal biphasic GA waveforms resulting from the biphasic GA waveforms for varying duration and timing of the anodic phase (the curves represent the mean of the cathodic phases of the waveforms across 5 trials of the GA, and waveforms were shifted to align the peaks).

The shapes of biphasic GA waveforms varied with both the timing and duration of the anodic phase. Most waveforms still resembled truncated normal curves, but the peaks of the cathodic phases were shifted away from the anodic phase (see FIG. 13). As with the monophasic GA waveforms, as $PW_{cathodic}$ increased the waveforms generally became flatter. The duration of the anodic phase relative to the cathodic phase influenced the peakedness of the resulting waveforms: the shorter the anodic phase, the sharper the peak of the cathodic phase. However, for waveforms with anodic phase first, $PW_{anodic}$=1 ms and $PW_{cathodic}$=0.2 or 0.1 ms, the peaks of the resulting waveforms were sharper than expected. Surprisingly, the peaks of both of these waveforms were located exactly 0.086 ms after the anodic pulse for every trial. Analysis of the gating parameters and membrane voltage during stimulation did not reveal any apparent explanations for this particular shape.

The biphasic GA waveforms were applied to five randomly selected populations from the population model, and energy-duration curves were calculated as in the monophasic case. Energy efficiencies of the biphasic GA waveforms as well as conventional waveforms were dependent on the timing and duration of the anodic phase (see FIGS. 14A and 14B). Conventional waveform shapes were paired with rectangular charge-balancing anodic phases with the same duration and timing as the biphasic GA waveforms, and the energy efficiencies of these waveforms were calculated in the population model. The biphasic GA waveforms were always more energy-efficient than the conventional waveform shapes, and the differences in energy efficiency varied with the duration of the anodic phase. In general, as $PW_{anodic}/PW_{cathodic}$ increased the difference in energy efficiency between the biphasic GA waveforms and the conventional waveform shapes decreased (see FIGS. 14C to 14H). As well, for $PW_{anodic}/PW_{cathodic}$=1 the differences between the biphasic GA waveforms and the conventional waveforms were generally greater than the differences in the monophasic case (FIGS. 8A to 8C), but for $PW_{anodic}/PW_{cathodic}$=10 the differences were smaller than in the monophasic case.

IV. Conclusion

The genetic algorithm (GA) described herein mimics biological evolution, to provide an optimal energy-efficient waveform shape for neural stimulation. The GA generates highly energy-efficient GA waveforms that resembled truncated Gaussian curves. When tested in computational models, and as confirmed by in vivo peripheral nerve stimulation, the GA waveforms are more energy-efficient than many conventional waveform shapes. The differences in energy-efficiency are more substantial for long PW s than for short PW s. The GA waveforms will extend the battery life of implantable stimulators, and thereby reduce the costs and risks associated with battery replacements, decrease the frequency of recharging, and reduce the volume of implanted stimulators.

Along with energy efficiency, the charge efficiency of stimulation is an important consideration with implanted devices. The charge delivered during a stimulus pulse contributes to the risk of tissue damage (Yuen et al. 1981; McCreery et al. 1990). Charge efficiency can be incorporated into the cost function, F (Equation (1)), with weights associated with charge and energy efficiency that reflected the relative importance of each factor. Charge efficiency was not considered in F in the GA described herein. Nevertheless, the GA waveforms ended up being simultaneously energy- and charge-efficient.

In the computational models, the GA waveforms were the most energy-efficient waveform shapes. All five independent trials of the GA converged to nearly the same shape for each PW and achieved similar levels of energy efficiency. In addition, all GA waveforms resemble truncated Gaussian curves, and none of the variations in the parameters of the GA had substantial effects on the outcome.

The energy efficiencies of non-GA Gaussian or sinusoids have been investigated previously. Sahin and Tie (2007) found in a computational model of a mammalian myelinated axon (Sweeney et al. 1987) that Gaussian and sinusoid waveforms had the lowest threshold energies out of several conventional waveform shapes. However, unlike the GA waveforms described herein, the Gaussian and sinusoid waveforms were not the most energy-efficient waveforms across all PWs. Qu et al. (2005) conducted in vitro experiments on rabbit hearts and found that defibrillation was achieved with significantly less energy for Gurvich (biphasic sinusoid) waveforms than with biphasic decaying exponential or rectangular waveforms. Dimitrova and Dimitrov (1992) found in a model of an unmyelinated Hodgkin-Huxley axon that waveforms that resembled postsynaptic potentials (skewed Gaussian) were more energy-efficient than rectangular waveforms. Although these previous studies showed that the sinusoid, Gaussian, or skewed Gaussian waveforms were more energy-efficient than other waveform shapes, these non-GA waveforms were not proven to be energy-optimal.

The GA with genes representing the parameters of the piece-wise generalized normal distribution (Equation (4))

did not produce GA waveforms with noticeably different shapes. However, the waveforms were much smoother, and for long PWs the tails were much closer to zero. These differences improved the energy efficiency over the original GA waveforms, particularly for long PW s. As a result, the energy-duration curve was no longer concave up, as in the original GA (see FIG. SA), but instead E never increased as PW increased. This result is more consistent with expectations; one would expect that at a given PW the GA could produce any waveform that was produced at a shorter PW bounded by tails of zero amplitude. Therefore, as PW increases E should either level off or decrease.

The different properties of the MRG axon and the Hodgkin-Huxley axon led to the dissimilarities in the genetically—optimized waveforms produced in the two models. Not only were the differences in ion channel dynamics between the two models substantial, but also the Hodgkin-Huxley axon lacked paranodal sections, and both factors likely contributed to the differences in GA waveforms. However, due to the non-linearity and complexity of the equations governing membrane voltage, it is difficult to pinpoint which characteristics of the axonal models were most responsible for the varying results. Additional trials of the GA in models where specific geometric and physiological parameters were varied systematically could determine how energy-optimal waveforms change with model parameters. Thus, the GA approach can determine energy-optimal waveform shapes for a given model or system, but the optimal shape may be different in each case.

The biphasic GA waveforms exhibited many similarities to the monophasic GA waveforms. Both sets of GA waveforms were more energy-efficient than several conventional waveform shapes and were unimodal in shape. However, the peakedness and locations of the peaks of the biphasic GA waveforms were different than the monophasic GA waveforms. The effects of the anodic phase on the sodium channels explain many of the differences among the shapes of the biphasic GA waveforms. The anodic phase hyperpolarizes the membrane, deactivating m-gates and de-inactivating the h-gates of the sodium channel. When the cathodic phase was delivered first, the peak likely shifted away from the anodic phase to activate the sodium channels earlier than in the monophasic case, thus offsetting the deactivation generated by the anodic phase. When the anodic phase was delivered first, the peak shifted away from the anodic phase to allow the m-gate of the sodium channels to return to baseline. Differences between the monophasic and biphasic GA waveforms were greater for short $PW_{anodic}$ than for long $PW_{anodic}$. As $PW_{anodic}$ increased, the amplitude of the anodic phase decreased, reducing the effect of the anodic phase on membrane voltage and the sodium channels. Consequently, the biphasic GA waveforms began to resemble the monophasic GA waveforms in both shape and energy efficiency.

The foregoing description describes the energy and charge efficiency for excitation of peripheral nerve fibers. Still, the technical features of the GA waveforms pertain to stimulation of other components of the nervous system. During spinal cord stimulation, the targets of stimulation are thought to be axons (Coburn 1985; Struijk et al. 1993; Struijk et al. 1993), and the current findings would likely be applicable. As well, our results would be valid for muscular stimulation, where the targets of stimulation are motor nerve axons (Crago et al. 1974). The technical features for the GA waveforms as described herein can also be relevant for stimulation of the brain because in both cortical stimulation (Nowak and Bullier 1998; Manola et al. 2007) and deep brain stimulation (McIntyre and Grill 1999), the targets of stimulation are thought to be axons.

GA waveforms could substantially increase the battery life of implanted stimulators. For example, the stimulators used for deep brain stimulation last approximately 36-48 months with conventional waveforms (Ondo et al. 2007). Over 30 years, the device would have to be replaced about 8-10 times. Over a clinically relevant range of PWs (~0.05-0.2 ms) the GA waveforms were upwards to approximately 60% more energy-efficient than either the rectangular or decaying exponential waveforms, which are the most frequently used waveforms clinically (Butson and McIntyre 2007). A 60% improvement in energy efficiency would extend battery life by over 21 months. As a result, over 30 years the device would only have to be replaced about 5-6 times.

The GA described herein did not account for the energy consumed by the electronic circuitry of an implantable stimulator. A stimulation waveform that can be generated using a simple analog circuit may consume less energy than a waveform that requires several active components. If the energy consumption of the circuitry were incorporated into the GA, then the algorithm may produce different waveform shapes.

Various features of the invention are set forth in the claims that follow.

Appendix 1. Conventional Waveform Shapes

Thresholds were measured for conventional waveforms used in neural stimulation: rectangular, rising/decreasing ramp, rising/decaying exponential, and sine wave. For all shapes, stimulation was applied at t=0 and turned off at t=PW. The equation for the stimulus current with the rectangular waveform was $$I_{stim}(t) = K_s * [u(t) - u(t-PW)] \quad \text{Equation (6)}$$

where $K_s$ is the current amplitude, t is time, and u(t) is the unit step function. The equations for the rising and decreasing ramp were $$I_{stim}(t) = K_r * [u(t) - u(t-PW)] \quad \text{Equation (7)}$$

$$I_{stim}(t) = K_r(PW-t) * [u(t) - u(t-PW)] \quad \text{Equation (8)}$$

respectively, where $K_r$ is the magnitude of the slope of the ramp. The equations for the rising and decaying exponential waveforms were $$I_{stim}(t) = K_e e^{t/\tau} * [u(t) - u(t-PW)] \quad \text{Equation (9)}$$

$$I_{stim}(t) = K_e e^{(PW-t)/\tau} * [u(t) - u(t-PW)] \quad \text{Equation (10)}$$

respectively, where $K_e$ is the amplitude at t=0 for Equation (9) and at t=PW for Equation (10). In the computational models, $\tau$ equaled 263 µs. The equation for the sine wave was $$I_{stim}(t) = K_{sin} * \sin\left(\frac{t}{PW}\pi\right) * [u(t) - u(t-PW)] \quad \text{(Equation 11)}$$

where $K_{sin}$ is the amplitude of the sine wave. Note that only one half of one period of the sine wave is delivered during the pulse.

2. Skewness and Kurtosis of Piece-Wise Generalized Normal Distribution

To quantify the shape of the GA waveforms, the waveforms were fitted to a piece-wise generalized normal distribution, f(t) (4), and calculated the skewness and kurtosis. First, the peak was centered about t=0:

$$\tau = t - \mu \quad \text{Equation (12)}.$$

Then, f(τ) was normalized so the time integral from −∞ to +∞ equaled 1:

$$N = \int_{-\infty}^{\infty} f(\tau) d\tau \quad \text{Equation (13)}$$
$$= \int_{-\infty}^{0} f_L(\tau) d\tau + \int_{0}^{\infty} f_R(\tau) d\tau$$
$$= \alpha_L \Gamma\left(1 + \frac{1}{\beta_L}\right) + \alpha_R \Gamma\left(1 + \frac{1}{\beta_R}\right)$$

$$F(\tau) = f(\tau)/N \quad \text{Equation (14)}$$

Next, the mean and variance of the distribution were calculated:

$$\bar{\tau} = \int_{-\infty}^{\infty} \tau * F(\tau) d\tau \quad \text{Equation (15)}$$
$$= \frac{-\alpha_L^2\left(1 + \frac{2}{\beta_L}\right) + \alpha_R^2 \Gamma\left(1 + \frac{2}{\beta_R}\right)}{2N}$$

$$\sigma 2 = \int_{-\infty}^{\infty} (\tau - \bar{\tau})^2 * F(\tau) d\tau \quad \text{Equation (16)}$$
$$= \frac{\begin{array}{l}3\alpha_L \bar{\tau}^2 \Gamma\left(1 + \frac{1}{\beta_L}\right) + 3\alpha_L^2 \bar{\tau} \Gamma\left(1 + \frac{2}{\beta_L}\right) + \\ \alpha_L^3 \Gamma\left(1 + \frac{3}{\beta_L}\right) + 3\alpha_R \bar{\tau}^2 \Gamma\left(1 + \frac{1}{\beta_R}\right) - \\ 3\alpha_R^2 \bar{\tau} \Gamma\left(1 + \frac{2}{\beta_R}\right) + \alpha_R^3 \Gamma\left(1 + \frac{3}{\beta_R}\right)\end{array}}{3N}.$$

Finally, from these equations, skewness and kurtosis were calculated:

$$\text{skew} = \frac{\int_{-\infty}^{\infty} (\tau - \bar{\tau})^3 * F(\tau) d\tau}{(\sigma^2)^{2/2}} \quad \text{Equation (17)}$$

$$\text{kurt} = \frac{\int_{-\infty}^{\infty} (\tau - \bar{\tau})^4 * F(\tau) d\tau}{(\sigma^2)^2}. \quad \text{Equation (18)}$$

Having thus described the invention, we claim:

1. A system for creating and applying a stimulation waveform optimized for energy efficiency comprising:
   a population of parent stimulation waveforms;
   a genetic algorithm (GA) for generating a population of offspring stimulation waveforms by mating the population of parent stimulation waveforms,
   a computational model of extracellular stimulation of a mammalian myelinated axon, being operative for assessing the fitness of individual offspring stimulation waveforms generated by the genetic algorithm in terms of energy efficiency and selecting as a new population of the parent stimulation waveforms the current offspring stimulation waveforms having the highest energy efficiency values, the selection terminating when predetermined termination criteria is met to provide an optimized stimulation waveform, and
   an implantable pulse generator being operable to apply the optimized stimulation waveform.

2. The system of claim 1, wherein the implantable pulse generator comprises a programmable microprocessor.

3. The system of claim 2, wherein the programmable microprocessor comprises embedded code.

4. The system of claim 3, wherein the embedded code comprises pre-programmed rules under which desired electrical stimulation is generated.

5. The system of claim 1 further comprising a lead operable connected with the implantable pulse generator.

6. The system of claim 5, wherein the lead comprises an electrode through which electrical stimulation is applied to targeted tissue region.

7. The system of claim 1, wherein the implantable pulse generator comprises a battery.

* * * * *